US 7,776,545 B2

(12) United States Patent
Khosla et al.

(10) Patent No.: US 7,776,545 B2
(45) Date of Patent: Aug. 17, 2010

(54) DIAGNOSTIC METHOD FOR CELIAC SPRUE

(75) Inventors: Chaitan Khosla, Palo Alto, CA (US); Lu Shan, Houston, TX (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1144 days.

(21) Appl. No.: 10/531,547

(22) PCT Filed: Nov. 20, 2003

(86) PCT No.: PCT/US03/37434

§ 371 (c)(1),
(2), (4) Date: Nov. 16, 2005

(87) PCT Pub. No.: WO2004/045392

PCT Pub. Date: Jun. 3, 2004

(65) Prior Publication Data
US 2006/0240475 A1  Oct. 26, 2006

Related U.S. Application Data

(60) Provisional application No. 60/428,033, filed on Nov. 20, 2002.

(51) Int. Cl.
G01N 33/53  (2006.01)
(52) U.S. Cl. ..................................... 435/7.1
(58) Field of Classification Search .................. 435/7.1, 435/7.2, 7.91, 7.92
See application file for complete search history.

(56) References Cited

U.S. PATENT DOCUMENTS

| 4,203,967 A | | 5/1980 | Gallo-Torres | |
|---|---|---|---|---|
| 4,656,253 A | * | 4/1987 | Lewicki | 435/7.94 |
| 4,912,120 A | | 3/1990 | Castelhano et al. | |
| 4,929,630 A | | 5/1990 | Castelhano et al. | |
| 5,817,523 A | | 10/1998 | Picarelli | |
| 5,834,428 A | | 11/1998 | Drucker | |
| 6,197,356 B1 | | 3/2001 | Girsh | |
| 6,294,320 B1 | * | 9/2001 | Hruska et al. | 435/4 |
| 6,319,726 B1 | | 11/2001 | Schuppan | |
| 6,410,550 B1 | | 6/2002 | Coe | |
| 7,144,569 B1 | | 12/2006 | Anderson et al. | |
| 7,202,216 B2 | | 4/2007 | Sollid et al. | |
| 7,303,871 B2 | * | 12/2007 | Hausch et al. | 435/6 |
| 7,462,688 B2 | | 12/2008 | Khosla et al. | |
| 2001/0007690 A1 | | 7/2001 | Girsh | |
| 2001/0036639 A1 | | 11/2001 | Fine | |
| 2002/0039599 A1 | | 4/2002 | Lin et al. | |
| 2002/0076834 A1 | | 6/2002 | Detlef et al. | |
| 2003/0215438 A1 | | 11/2003 | Hausch | |
| 2004/0241664 A1 | | 12/2004 | Dekker et al. | |
| 2006/0052308 A1 | | 3/2006 | Khosla et al. | |
| 2006/0178299 A1 | | 8/2006 | Anderson et al. | |
| 2006/0240475 A1 | | 10/2006 | Khosla et al. | |
| 2008/0299108 A1 | | 12/2008 | Khosla et al. | |
| 2009/0156490 A1 | | 6/2009 | Khosla et al. | |

FOREIGN PATENT DOCUMENTS

| EP | 0237082 | | 9/1987 |
|---|---|---|---|
| EP | 0 905 518 A1 | | 3/1999 |
| WO | WO 94/26774 | | 11/1994 |
| WO | 96/10034 | | 4/1996 |
| WO | 00/42213 | | 7/2000 |
| WO | 01/25793 | | 4/2001 |
| WO | WO 01/25793 A2 | | 4/2001 |
| WO | 01/25793 | | 12/2001 |
| WO | WO 03/068170 | | 8/2003 |
| WO | 03/096984 | | 11/2003 |
| WO | WO 03104273 | * | 12/2003 |
| WO | 2004/045392 | | 6/2004 |
| WO | 2005/049064 | | 6/2005 |

OTHER PUBLICATIONS

Arentz-Hansen et al. (Gut 2000 vol. 46, p. 46-51).*
Garcia-Maroto et al. (Plant Molecular Biol 1990 vol. 14, p. 867-868).*
Campbell (section 1.3.4.; p. 1-32; Monoclonal Antibody Technology (1984) Elsevier Science Publishers).*
Ahnen et al., Intestinal Aminooligopeptidase. In Vivo Synthesis on Intracellular Membranes of Rat Jejunum, 1982, J. Biol. Chem., 257, 12129-35.
Arentz-Hansen et al., The Intestinal T Cell Response to β-Gliadin in Adult Celiac Disease is Focused on a Single Deamidated Glutamine Targeted by Tissue Transglutaminase, 2000, J. Exp. Med., 191, 603-12.
Bordusa et al., The Specificity of Prolyl Endopeptidase From Flavobacterium Meningoseptum: Mapping the S' Subsites by Positional Scanning Via Acyl Transfer,1998, Bioorg. Med. Chem., 6, 1775-80.
Colot et al., The Genes Encoding Wheat Storage Proteins: Towards a Molecular Understanding of Bread-Making Quality and Its Genetic Manipulation, 1990, Genet Eng,, 12:225-41.
Database Derwent, ACC-No. 1996-329479, HLA-Binding Oligopeptide and an Immuno: Regulator CONTGIT—Used in the Treatment of Auto: Immune Disease, 1999.
Lahteenoja et al., Local Challenge on Oral Mucosa With an Alpha-Gliadin Related Synthetic Peptide in Patients With Celiac Disease, 2000, Am. J. Gastroenterol., 95: 2880.
Schuppan, Current Concepts of Celiac Disease Pathogenesis, 2000, Gastroenterology, 119, 234-42.
Wieser, The Precipitating Factor in Coeliac Disease, 1995, Baillieres Clin Gastroenterol, 9(2):191-207.
Wieser, 1996, Relation Between Structure an Dcoeliac Toxicity, Acta Paediatr Suppl., 412:3-9.

(Continued)

*Primary Examiner*—Jacob Cheu
(74) *Attorney, Agent, or Firm*—Bozicevic, Field & Francis LLP; Pamela J. Sherwood

(57) ABSTRACT

Detection of toxic gluten oligopeptides refractory to digestion and antibodies and T cells responsive thereto can be used to diagnose Celiac Sprue.

6 Claims, 8 Drawing Sheets

OTHER PUBLICATIONS

Yoshimoto et al., Prolyl Endopeptidase From Flavobacterium Meningosepticum: Cloning and Sequencing of the Enzyme Gene, 1991, J. Biochem., 110, 873-8.

Arentz-Hansen et al. "Celiac Lesion T Cells Recognizes Epitopes that Cluster in Regions of Gliadins Rich in Proline Residues" Gastroenterology, 2002, pp. 803-809, vol. 123, No. 3.

Arentz-Hansen et al., "The Intestinal T Cell Response To a β-Gliadin in Adult Celiac Disease Is Focused On A Single Deamidated Glutamine Targeted by Tissue Transglutaminase" J. Exp. Med., 2000, pp. 603-612, Vol. 191.

Castelhano et al., "Synthesis, Chemistry, and Absolute Configuratin of Novel Transglutaminiase Inhibitors Containing a 3-Halo-4,5-dihydroisoxazole" Bioorg. Chem., 1988, pp. 335-340, vol. 16.

de Ritis G. et al. "In Vitro (organ culture) Studies of the Toxicity of Specific A-Gliadin Peptides in celiac Disease" Gastroenbterology, 1988, pp. 41-49, vol. 94.

Frazer et al. "Gluten-induced enteropathy: the effect of partially digested gluten." Lancet, Sep. 5, 1959, pp. 252-5, vol. 2.

Freund, K. et al. "Transglutaminase inhibition by 2-[(2-Oxopropyl)thio]imidazolium derivatives: mechanism of factor XIIIa inactivation" Biochemistry, 1994, pp. 10109-10119, vol. 33.

Greenberg, C. et al. "Transglutaminases: multifunctional cross-linking enzymes that stabilize tissues" FASEB J., 1991, pp. 3071-3077, vol. 5.

Hitomi, K. et al. "GTP, an inhibitor of transglutaminases, is hydrolyzed by tissue-type transglutaminase (TGase 2) but not by epidermal-type transglutaminase (TGase 3)," Biosci. Biotechnol. Biochem., 2000, pp. 657-659, vol. 64, Issue 3.

Kao Castle Pty LTD Sequence Analysis PCTRIS03104743.

Karpuj et al. "Prolonged survival and decreased abnormal movements in transgenic model of Huntington disease, with administration of the transglutaminase inhibitor cystamine" Nature Med., Feb. 2002, pp. 143-149, vol. 8, Issue 2.

Kim et al. "Transglutaminases in disease" Neurochem. Int., 2002, pp. 85-103, vol. 40.

Lion. Flavobacterium meningosepticum. Genbank Accession #/EMBL #: D10980. Aug. 1, 1992. http://www.infobiogen.fr/srs71bin/cgi-bin/wgetz?-id+4jqa61Mc9PO+[uniprot-ID:PPCE_FLAME]+-e.

Lorand et al. "Novel inhibitors against the transglutaminase-catalysed crosslinking of lens proteins" Exp Eye Res., May 1998, pp. 531-536, vol. 66.

Messer et al. "Studies On The Mechanism Of Destruction Of The Toxic Action Of Wheat Gluten In Coeliac Disease By Crude Papain" Gut., Aug. 1964, pp. 295-303, vol. 5.

Messer et al."Oral papain in gluten intolerance." Lancet, Nov. 6, 1976, p. 1022, vol. 2, Issue 7993.

Moodie, P. "Traditional Baking Enzymes-Proteases" Presented at the American Institute of Baking, Manhattan, Kansas, May 7, 2001 by Peter Moodie, Director—Sales & Marketing, Enzyme Development Corporation, Enzyme Development Corporation.

Online-Medical Dictionary. "Amino acid". http://cancerweb.ncl.ac.uk/cgi-bin/omd?query=amino+acid. Nov. 13, 1997.

Piper et al., "High selectivity of human tissue transglutaminase for immunoactive gliadin peptides: implications for celiac spure", Biochemistry, Jan. 8, 2002, pp. 386-393, vol. 41, Issue 1.

Sárdy, M. et al. "Epidermal transglutaminase (TGase 3) is the autoantigen of dermatitis herpetiformis" J. Exp. Med., 2002, pp. 747-757, vol. 195, Issue 6.

Shan, L. et al. "Structural Basis for Gluten Intolerance in Celiac Sprue" Science 2002, pp. 2275-2279, vol. 297.

Sjostrom et al. "Identification of a Gliadin T-Cell Epitope in Coeliac Disease: General Importance of Gliadin Deamidation for Intestinal T-Cell Recognition" Scandinavian Journal of Immunology, Aug. 1998, pp. 111-115(5), vol. 48, No. 2.

Vader et al. "The Gluten Response in Children with Celiac Sprue Disease is Directed Toward Multiple Gliadin and Glutenin Peptides" Gastroenterology, 2002, pp. 1729-1737, vol. 122.

Smith; et al., "Abnormal expression of dipeptidylpeptidase IV activity in enterocyte brush-border membranes of children suffering from coeliac disease", Experimental Physiology, Jul. 1990, 75(4):613-616.

Wruble, Milton, "Enteric Coating. I. A Laboratory Method for the Study and Control of Enteric Coatings", Journal of the American Pharmaceutical Association, Jul. 1935, XXIV(7):570-574.

Auger; et al., "Solid-State 13C NMR Study of a Transglutaminase-Inhibitor Adduct", Biochemistry (1993), 32:3930-3934.

Cornell; et al., "In vitro mucosal digestion of synthetic gliadin-derived peptides in celiac disease", Journal of Protein Chemistry (1995), 14(5):335-339.

Goldsmith; et al., "Inhibition of Human Epidermal Transglutaminases In-Vitro and In-Vivo by Tyrosineamidomethyldihydrohaloisoxazoles", Journal of Investigative Dermatology (1991), 97(1):156-158.

Killackey; et al., "A New Class of Mechanism-Based Inhibitors of Translutaminase Enzymes Inhibits the Formation of Cross-Linked Envelopes by Human Malignant Keratinocytes", Molecular Pharmacology (1989), 35(5):701-706.

Piper; et al., "Effect of Prolyl Endopeptidase on Digestive-Resistant Gliadin Peptides in Vivo", Journal of Pharmacology and Experimental Therapeutics (2004), 311(1):213-219.

Shan; et al., "Comparative biochemical analysis of three bacterial prolyl endopeptidases: Implications for celiac sprue", Biochemical Journal (2004), 382(2):311-318.

Watts; et al., "Structure-activity relationship analysis of the selective inhibition of transglutaminase 2 by dihydroisoxazoles", Journal of Medicinal Chemistry (2006), 49(25):7493-7501.

Qiao; et al., "Antigen presentation to celiac lesion-derived T cells of a 33-mer gliadin peptide naturally formed by gastrointestinal digestion", Journal of Immunology (2004), 173(3):1757-1762.

Xia; et al., Equilibrium and kinetic analysis of the unusual binding behavior of a highly immunogenic gluten peptide to HLA-DQ2, Biochemistry (2005), 44(11):4442-4449.

* cited by examiner

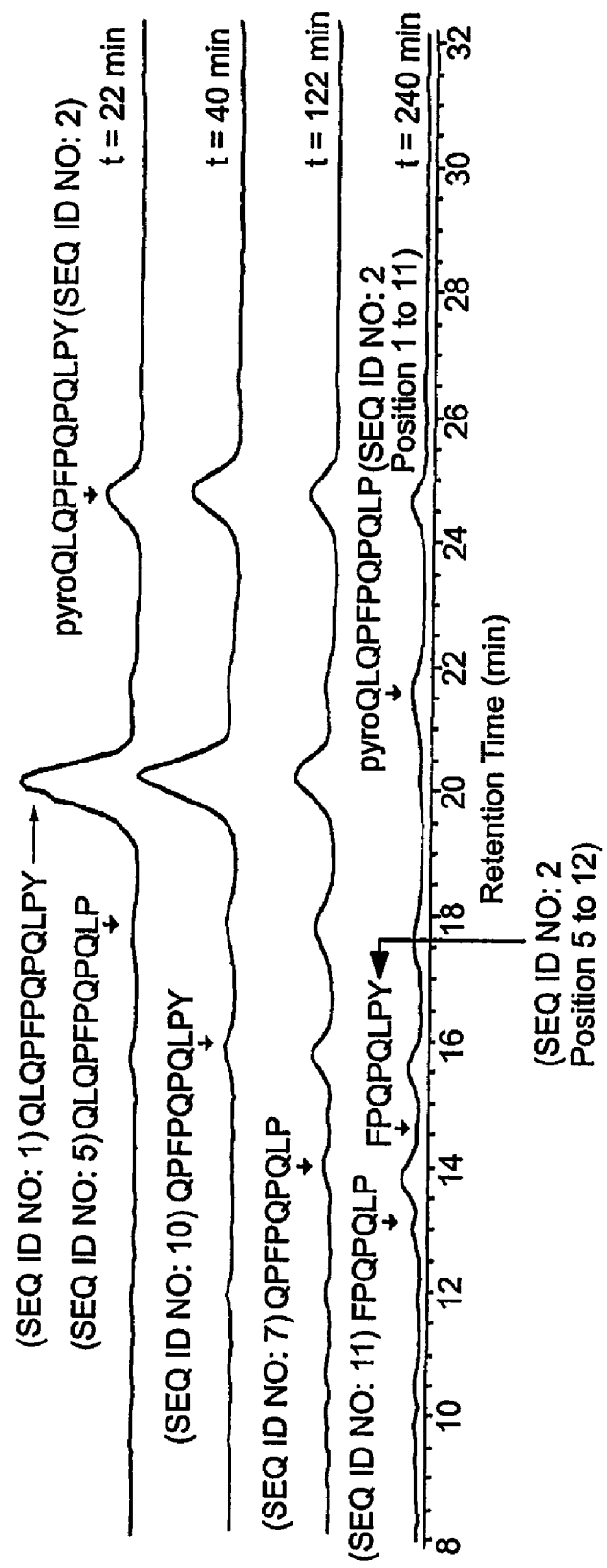

DIAGNOSTIC METHOD FOR CELIAC SPRUE

FEDERALLY-SPONSORED RESEARCH OR DEVELOPMENT

This invention was made with Government support under contract 9910949 awarded by the National Science Foundation. The Government has certain rights in this invention.

In 1953, it was first recognized that ingestion of gluten, a common dietary protein present in wheat, barley and rye causes disease in sensitive individuals. Gluten is a complex mixture of glutamine- and proline-rich glutenin and prolamine molecules, which is thought to be responsible for disease induction. Ingestion of such proteins by sensitive individuals produces flattening of the normally luxurious, rug-like, epithelial lining of the small intestine known to be responsible for efficient and extensive terminal digestion of peptides and other nutrients. Clinical symptoms of Celiac Sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European populations.

A related disease is dermatitis herpetiformis, which is a chronic eruption characterized by clusters of intensely pruritic vesicles, papules, and urticaria-like lesions. IgA deposits occur in almost all normal appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine and colchicines are sometimes prescribed for relief of itching.

Celiac Sprue is generally considered to be an autoimmune disease and the antibodies found in the serum of the patients support a theory of an immunological nature of the disease. Antibodies to tissue transglutaminase (tTG) and gliadin appear in almost 100% of the patients with active CS, and the presence of such antibodies, particularly of the IgA class, has been used in diagnosis of the disease.

The large majority of patients express the HLA-DQ2 [DQ (a1*0501, b1*02)] and/or DQ8 [DQ(a1*0301, b1*0302)] molecules. It is believed that intestinal damage is caused by interactions between specific gliadin oligopeptides and the HLA-DQ2 or DQ8 antigen, which in turn induce proliferation of T lymphocytes in the sub-epithelial layers. T helper 1 cells and cytokines apparently play a major role in a local inflammatory process leading to villous atrophy of the small intestine.

At the present time there is no good therapy for the disease, except to completely avoid all foods containing gluten. Although gluten withdrawal has transformed the prognosis for children and substantially improved it for adults, some people still die of the disease, mainly adults who had severe disease at the outset. An important cause of death is lymphoreticular disease (especially intestinal lymphoma). It is not known whether a gluten-free diet diminishes this risk. Apparent clinical remission is often associated with histologic relapse that is detected only by review biopsies or by increased EMA titers.

Gluten is so widely used, for examples in commercial soups, sauces, ice creams, hot dogs, etc., that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

Current diagnostic methods for Celiac Sprue are expensive and not very accurate. These methods include ELISA-based methods in which either anti-gliadin or anti-tTG antibodies in the patient's serum are detected and in which T cell proliferation upon stimulation with gliadin is observed. Often, however, these methods are not sensitive enough to detect the diagnostic antibodies in the blood or, as is the case for T cell proliferation assays, are deemed to be too expensive for routine use. Typically, even if an individual tests positive in the diagnostic test, the individual must be re-challenged with gliadin (typically after maintaining a gluten-free diet for an extended period of time) and examined by endoscopy, an invasive and often painful procedure.

PCT publication No. WO 01/25793, published 12 Apr. 2001, describes peptides derived from epitope mapping of alpha-gliadin and methods for diagnosing Celiac Sprue using such peptides. Those methods, however, do not appear to be significantly more sensitive than methods currently employed and so do not overcome the limitations of diagnostic methods currently in use.

PCT publication No. WO 02/083722 describes HLA-DQ restricted T cells receptors capable of recognizing prolamine-derived peptides involved in food-related immune enteropathy.

There remains a need for better diagnostic methods for Celiac Sprue, methods that are more sensitive than current methods, that do not require confirmation by endoscopy, and that do not require that an individual be challenged with a gluten-containing diet for accuracy. The present invention addresses this need.

SUMMARY OF THE INVENTION

Methods are provided for diagnosing Celiac Sprue, and/or dermatitis herpetiformis, by detecting multivalent toxic gluten oligopeptides in a patient; antibodies that bind to the toxic gluten oligopeptides; or T cell proliferation elicited by such oligopeptides in a patient. Multivalent toxic gluten oligopeptides have been found to be resistant to cleavage by gastric and pancreatic enzymes, and the presence of such peptides results in toxic effects mediated by antibodies and T cell proliferation. By providing methods for detecting the toxic gluten oligopeptides and the toxic effects mediated thereby, improved diagnostic methods for diagnosing Celiac Sprue are provided.

BRIEF DESCRIPTION OF THE DRAWINGS

FIGS. 1A-1B. Brush border membrane catalyzed digestion of the immunodominant gliadin peptide. FIG. 1A: LC-MS traces of SEQ ID NO:1 QLQPFPQPQLPY after digestion with 27 ng/µl rat brush border membrane (BBM) protein for the indicated time. Reaction products were separated by reversed phase HPLC and detected by mass spectroscopy (ion counts m/z=300-2000 g/mol). The indicated peptide fragments were confirmed by characteristic tandem MS fragmentation patterns. The SEQ ID NO:2 pyroQLQPFPQPQLPY peak corresponds to an N-terminally pyroglutaminated species, which is generated during HPLC purification of the synthetic starting material. FIG. 1B Abundance of individual digestion products as a function of time. The peptide fragments in FIG. 1A were quantified by integrating the corresponding MS peak area (m/z=300-2000 g/mol). The resulting MS intensities are plotted as a function of digestion time (with BBM only, colored bars). The digestion experiment was repeated in the presence of exogenous DPP IV from *Aspergillus fumigatus* (Chemicon International, CA, 0.28 µU DPP IV/ng BBM protein) and analyzed as above (open bars). The relative abundance of different intermediates could be estimated from the $UV_{280}$ traces and control experiments using authentic standards. The inserted scheme shows an interpretative diagram of the digestion pathways of (SEQ ID NO:1) QLQPFPQPQLPY and its intermediates, the BBM peptidases involved in each step, and the amino acid residues that are released. The color code for labeling the peptides is similar to that used in A. The preferred breakdown pathway is indicated in bold. APN=aminopeptidase N, CPP=carboxypeptidase P, DPP IV=dipeptidyl dipeptidase IV.

FIG. 2A: (SEQ ID NO:3) PQPQLPYPQPQLPY was digested by 27 ng/µl brush border membrane (BBM) protein preparations for the indicated time and analyzed as in FIG. 1A. The identity of the starting material and the product (SEQ ID NO:4) PQPQLPYPQPQLP was corroborated by MSMS fragmentation. The intrinsic mass intensities of the two peptides were identical, and the $UV_{280}$ extinction coefficient of (SEQ ID NO:4) PQPQLPYPQPQLP was half of the starting material in accordance with the loss of one tyrosine. All other intermediates were below ≧1%. The scheme below shows the proposed BBM digestion pathway of (SEQ ID NO:3) PQPQLPYPQPQLPY with no observed N-terminal processing (crossed arrow) and the removal of the C-terminal tyrosine by carboxypeptidase P (CPP) in bold. Further C-terminal processing by dipeptidyl carboxypeptidase (DCP) was too slow to permit analysis of the subsequent digestion steps (dotted arrows). FIG. 2B: Influence of dipeptidyl carboxypeptidase on C-terminal digestion. (SEQ ID NO:3) PQPQLPYPQPQLPY in phosphate buffered saline:Tris buffered saline=9:1 was digested by BBM alone or with addition of exogenous rabbit lung DCP (Cortex Biochemicals, CA) or captopril. After overnight incubation, the fraction of accumulated SEQ ID NO:4) PQPQLPYPQPQLP (compared to initial amounts of (SEQ ID NO:3) PQPQLPYPQPQLPY at t=0 min) was analyzed as in FIG. 2A, but with an acetonitrile gradient of 20-65% in 6-35 minutes.

DETAILED DESCRIPTION OF THE EMBODIMENTS

Figure 1B:
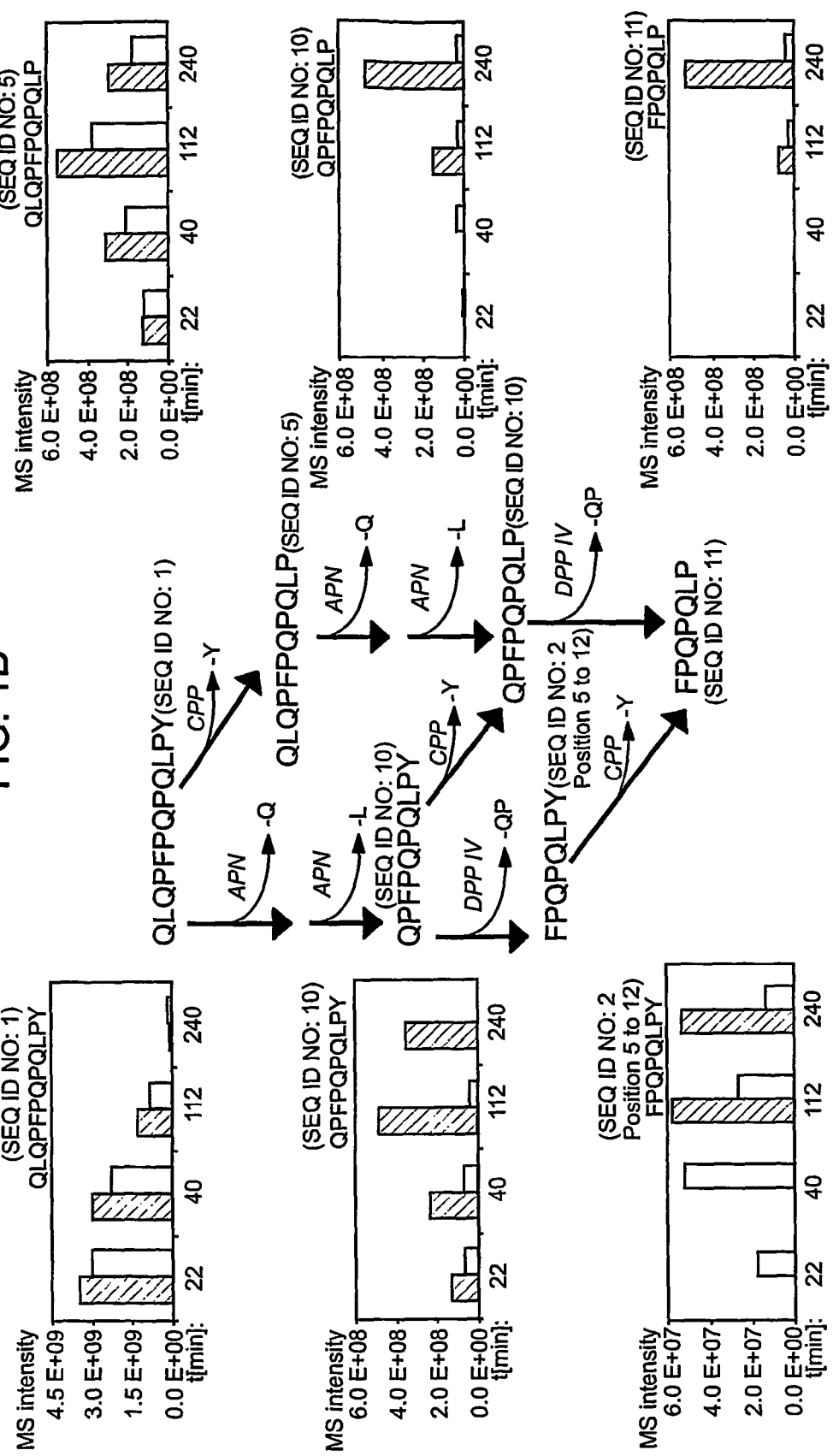

Celiac Sprue and/or dermatitis herpetiformis are diagnosed by detecting digestion-refractory multivalent gluten oligopeptides, antibodies that bind to such gluten oligopeptides and/or T-cell proliferation produced by such oligopeptides in Celiac Sprue individuals. Gluten oligopeptides are highly resistant to cleavage by gastric and pancreatic peptidases such as pepsin, trypsin, chymotrypsin, and the like. Some of these peptides are multivalent, in that they comprise multiple T cell and/or antibody recognition epitopes. The natural covalent linkage of these epitopes in a polypeptide is a determinant of hyperantigenicity in susceptible individuals, and related to disease development and pathology. By providing for detection of such gluten oligopeptides; of antibodies specifically reactive thereto; and/or of T-cell proliferation produced by such oligopeptides in individuals, improved methods of diagnosing Celiac Sprue and/or dermatitis herpetiformis are provided.

The present invention arose in part from the discovery of a 33-mer gliadin oligopeptide that is refractory to digestion and is a substrate for tTGase. The selectively deamidated 33-mer produced by tTGase action is a potent activator of T cells. The experimental analyses that led to the discovery of this 33-mer are described in the Examples below. In Example 1, a variety of immunodominant epitopes (see Arentz-Hansen et al. (2001), J. Exp. Med. 191:603-612) were tested for resistance to proteolytic enzymes encountered in digestion. Based in part on the results of the experiments of Example 1, an alpha-gliadin was subjected to similar tests, as described in Example 2. Those tests showed that a relatively large fragment of the gliadin protein was resistant to digestion by intestinal enzymes. This large fragment, which may be referred to as the 33-mer of the invention, has the sequence (SEQ ID NO:12) LQLQPFPQPQLPYPQPQLPYPQPQLPYPQPQPF.

Multivalent Gluten Oligopeptides

Preferably, antigenic gluten oligopeptides of interest for use in the methods of the invention are multivalent, and comprise multiple T cell or B cell epitopes, usually comprising at least about two epitopes, preferably at least about three epitopes, and where each epitope is either non-overlapping (i.e., sterically separate) or overlapping. In other words, a non-overlapping epitope refers to an epitope where the amino acids of a first epitope are not integral to the sequence of a second epitope and an overlapping epitope refers to an epitope where the amino acids of a first epitope are integral to the sequence of a second epitope. For oligopeptides comprising non-overlapping epitopes, each distinct epitope is separated from another epitope by at least a peptide bond, and may be separated by one or more amino acids. As used herein, the term "epitope" refers to the portion of an antigen bound by an antibody or T cell receptor, which portion is sufficient for high affinity binding. In polypeptide antigens, generally a linear epitope for recognition will be at least about 7 amino acids in length, and may be 8 amino acids, 9 amino acids, 10 amino acids, or more.

Generally, the oligopeptides comprise a sequence that may be represented by the formula:

$$E_1\text{-}X_1\text{-}E_2\text{-}X_2\text{-}E_3 \ldots X_n\text{-}E_y \quad (I)$$

where $E_1$, $E_2$ and $E_3$ are independently selected epitopes, which may be the same or different including, but not limited to, those having the amino acid sequence: (SEQ ID NO:10) PFPQPQLPY, (SEQ ID NO:18) PQPQLPYPQ, (SEQ ID NO:19) PQLPYPQPQ, (SEQ ID NO:20) PYPQPQLPY, (SEQ ID NO:21) PQPELPYPQ, (SEQ ID NO:22) PFPQPELPY, (SEQ ID NO:23) PQQSFPQQQ, (SEQ ID NO:24) PFPQQPQQPFP, (SEQ ID NO:25) PYPQPELPY, and conservatively modified variants thereof, where $X_1$ and $X_2$ are independently selected spacers, which may be the same or different and comprise a peptide bond or one or more amino acids, where n=0-5, and where y=0-5. If n=0 and y=0, then the oligopeptide comprises the structure: $E_1\text{-}X_1\text{-}E_2\text{-}X_2\text{-}E_3$. In one embodiment of the invention, the antigenic oligopeptide comprises SEQ ID NO:12, which has the epitopic structure (where $X_1$ and $X_2$ are peptide bonds):

| LQLQ | PFPQPQLPY | PQPQLPYPQ | PQLPYPQPQ | PF |
|------|-----------|-----------|-----------|-----|
|      | $E_1$     | $E_2$     | $E_3$     |     |

Those of skill in the art will understand that additional epitopes (e.g., $E_4$, $E_5$, $E_6$, etc.), each separated by an additional peptide bond or one or more amino acids (e.g., $X_3$, $X_4$, $X_5$, etc.), are within the scope of the present invention.

Alternatively, the oligopeptides comprise at least one epitope that overlaps with at least one other epitope. As such, in another embodiment of the present invention, $E_1$ and $E_2$ and/or $E_2$ and $E_3$ of Formula I are not separated by spacers such as $X_1$ and $X_2$, but instead contain at least one overlapping amino acid, preferably at least two or three amino acids, and more preferably at least four amino acids. Suitable overlapping epitopes include, but are not limited to, those having the amino acid sequence: (SEQ ID NO:10) PFPQPQLPY, (SEQ ID NO:18) PQPQLPYPQ, (SEQ ID NO:19) PQLPYPQPQ, (SEQ ID NO:20) PYPQPQLPY, (SEQ ID NO:21) PQPELPYPQ, (SEQ ID NO:22) PFPQPELPY, (SEQ ID NO:23) PQQSFPQQQ, (SEQ ID NO:24) PFPQQPQQPFP, (SEQ ID NO:25) PYPQPELPY, and conservatively modified variants thereof. Those of skill in the art will understand that oligopeptides comprising a combination of non-overlapping and overlapping epitopes (e.g., $E_1\text{-}X_1\text{-}E_2\text{-}E_3$, $E_1\text{-}E_2\text{-}X_2\text{-}E_3$, etc.) are within the scope of the present invention. For example, the antigenic oligopeptide can comprise SEQ ID NO:12, which has the epitopic structure $E_1\text{-}X_1\text{-}E_2\text{-}E_3$ (where $E_2$ is PQPQLPYPQ, $E_3$ is PYPQPQLPY, and $E_2$ and $E_3$ contain a four amino acid overlap, indicated in bold):

| LQLQ | PFPQPQLPY | PQPQLPYPQPQLPY | PQPQPF |
|------|-----------|----------------|--------|
|      | $E_1$     | $E_2\text{-}E_3$ |        |

While any combination of the elements comprising $E_1$, $E_2$, and $E_3$ may comprise the oligopeptides of the present invention, certain combinations are preferred. For example, for oligopeptides containing non-overlapping epitopes, wherein the epitopes are selected from the group consisting of (1) (SEQ ID NO:10) PFPQPQLPY, (2) (SEQ ID NO:18) PQPQLPYPQ, (3) SEQ ID NO:19) PQLPYPQPQ, (4) (SEQ ID NO:20) PYPQPQLPY, (5) (SEQ ID NO:21) PQPELPYPQ, (6) (SEQ ID NO:22) PFPQPELPY, (7) (SEQ ID NO:23) PQQSFPQQQ, (8) (SEQ ID NO:24) PFPQQPQQPFP, and (9) (SEQ ID NO:25) PYPQPELPY, the following oligopeptides or conservatively modified variants thereof are preferred:

| | | | | | | | | |
|---|---|---|---|---|---|---|---|---|
| 1; 1; 1 | 1; 1; 2 | 1; 1; 3 | 1; 1; 4 | 1; 1; 5 | 1; 1; 6 | 1; 1; 7 | 1; 1; 8 | 1; 1; 9 |
| 1; 2; 1 | 1; 3; 1 | 1; 4; 1 | 1; 5; 1 | 1; 6; 1 | 1; 7; 1 | 1; 8; 1 | 1; 9; 1 | 2; 1; 1 |
| 3; 1; 1 | 4; 1; 1 | 5; 1; 1 | 6; 1; 1 | 7; 1; 1 | 8; 1; 1 | 9; 1; 1 | 2; 2; 1 | 2; 2; 2 |
| 2; 2; 3 | 2; 2; 4 | 2; 2; 5 | 2; 2; 6 | 2; 2; 7 | 2; 2; 8 | 2; 2; 9 | 2; 3; 1 | 2; 3; 2 |
| 2; 3; 3 | 2; 3; 4 | 2; 3; 5 | 2; 3; 6 | 2; 3; 7 | 2; 3; 8 | 2; 3; 9 | 2; 4; 1 | 2; 4; 2 |
| 2; 4; 3 | 2; 4; 4 | 2; 4; 5 | 2; 4; 6 | 2; 4; 7 | 2; 4; 8 | 2; 4; 9 | 2; 5; 1 | 2; 5; 2 |
| 2; 5; 3 | 2; 5; 4 | 2; 5; 5 | 2; 5; 6 | 2; 5; 7 | 2; 5; 7 | 2; 5; 9 | 2; 6; 1 | 2; 6; 2 |
| 2; 6; 3 | 2; 6; 4 | 2; 6; 5 | 2; 6; 6 | 2; 6; 7 | 2; 6; 8 | 2; 6; 9 | 2; 7; 1 | 2; 7; 2 |
| 2; 7; 3 | 2; 7; 4 | 2; 7; 5 | 2; 7; 6 | 2; 7; 7 | 2; 7; 8 | 2; 7; 9 | 2; 8; 1 | 2; 8; 2 |
| 2; 8; 3 | 2; 8; 4 | 2; 8; 5 | 2; 8; 6 | 2; 8; 7 | 2; 8; 8 | 2; 8; 9 | 2; 9; 1 | 2; 9; 2 |
| 2; 9; 3 | 2; 9; 4 | 2; 9; 5 | 2; 9; 6 | 2; 9; 7 | 2; 9; 8 | 2; 9; 9 | 3; 2; 1 | 3; 2; 2 |
| 3; 2; 3 | 3; 2; 4 | 3; 2; 5 | 3; 2; 6 | 3; 2; 7 | 3; 2; 8 | 3; 2; 9 | 3; 3; 1 | 3; 3; 2 |
| 3; 3; 3 | 3; 3; 4 | 3; 3; 5 | 3; 3; 6 | 3; 3; 7 | 3; 3; 8 | 3; 3; 9 | 3; 4; 1 | 3; 4; 2 |
| 3; 4; 3 | 3; 4; 4 | 3; 4; 5 | 3; 4; 6 | 3; 4; 7 | 3; 4; 8 | 3; 4; 9 | 3; 5; 1 | 3; 5; 2 |
| 3; 5; 3 | 3; 5; 4 | 3; 5; 5 | 3; 5; 6 | 3; 5; 7 | 3; 5; 8 | 3; 5; 9 | 3; 6; 1 | 3; 6; 2 |
| 3; 6; 3 | 3; 6; 4 | 3; 6; 5 | 3; 6; 6 | 3; 6; 7 | 3; 6; 8 | 3; 6; 9 | 3; 7; 1 | 3; 7; 2 |
| 3; 7; 3 | 3; 7; 4 | 3; 7; 5 | 3; 7; 6 | 3; 7; 7 | 3; 7; 8 | 3; 7; 9 | 3; 8; 1 | 3; 8; 2 |
| 3; 8; 3 | 3; 8; 4 | 3; 8; 5 | 3; 8; 6 | 3; 8; 7 | 3; 8; 8 | 3; 8; 9 | 3; 9; 1 | 3; 9; 2 |
| 3; 9; 3 | 3; 9; 4 | 3; 9; 5 | 3; 9; 6 | 3; 9; 7 | 3; 9; 8 | 3; 9; 9 | 4; 2; 1 | 4; 2; 2 |
| 4; 2; 3 | 4; 2; 4 | 4; 2; 5 | 4; 2; 6 | 4; 2; 7 | 4; 2; 8 | 4; 2; 9 | 4; 3; 1 | 4; 3; 2 |
| 4; 3; 3 | 4; 3; 4 | 4; 3; 5 | 4; 3; 6 | 4; 3; 7 | 4; 3; 8 | 4; 3; 9 | 4; 4; 1 | 4; 4; 2 |
| 4; 4; 3 | 4; 4; 4 | 4; 4; 5 | 4; 4; 6 | 4; 4; 7 | 4; 4; 8 | 4; 4; 9 | 4; 5; 1 | 4; 5; 2 |
| 4; 5; 3 | 4; 5; 4 | 4; 5; 5 | 4; 5; 6 | 4; 5; 7 | 4; 5; 8 | 4; 5; 9 | 4; 6; 1 | 4; 6; 2 |
| 4; 6; 3 | 4; 6; 4 | 4; 6; 5 | 4; 6; 6 | 4; 6; 7 | 4; 6; 8 | 4; 6; 9 | 4; 7; 1 | 4; 7; 2 |
| 4; 7; 3 | 4; 7; 4 | 4; 7; 5 | 4; 7; 6 | 4; 7; 7 | 4; 7; 8 | 4; 7; 9 | 4; 8; 1 | 4; 8; 2 |
| 4; 8; 3 | 4; 8; 4 | 4; 8; 5 | 4; 8; 6 | 4; 8; 7 | 4; 8; 8 | 4; 8; 9 | 4; 9; 1 | 4; 9; 2 |
| 4; 9; 3 | 4; 9; 4 | 4; 9; 5 | 4; 9; 6 | 4; 9; 7 | 4; 9; 8 | 4; 9; 9 | 5; 2; 1 | 5; 2; 2 |
| 5; 2; 3 | 5; 2; 4 | 5; 2; 5 | 5; 2; 6 | 5; 2; 7 | 5; 2; 8 | 5; 2; 9 | 5; 3; 1 | 5; 3; 2 |
| 5; 3; 3 | 5; 3; 4 | 5; 3; 5 | 5; 3; 6 | 5; 3; 7 | 5; 3; 8 | 5; 3; 9 | 5; 4; 1 | 5; 4; 2 |
| 5; 4; 3 | 5; 4; 4 | 5; 4; 5 | 5; 4; 6 | 5; 4; 7 | 5; 4; 8 | 5; 4; 9 | 5; 5; 1 | 5; 5; 2 |
| 5; 5; 3 | 5; 5; 4 | 5; 5; 5 | 5; 5; 6 | 5; 5; 7 | 5; 5; 8 | 5; 5; 9 | 5; 6; 1 | 5; 6; 2 |
| 5; 6; 3 | 5; 6; 4 | 5; 6; 5 | 5; 6; 6 | 5; 6; 7 | 5; 6; 8 | 5; 6; 9 | 5; 7; 1 | 5; 7; 2 |
| 5; 7; 3 | 5; 7; 4 | 5; 7; 5 | 5; 7; 6 | 5; 7; 7 | 5; 7; 8 | 5; 7; 9 | 5; 8; 1 | 5; 8; 2 |
| 5; 8; 3 | 5; 8; 4 | 5; 8; 5 | 5; 8; 6 | 5; 8; 7 | 5; 8; 8 | 5; 8; 9 | 5; 9; 1 | 5; 9; 2 |
| 5; 9; 3 | 5; 9; 4 | 5; 9; 5 | 5; 9; 6 | 5; 9; 7 | 5; 9; 8 | | | |

-continued

| | | | | | | | | | | |
|---|---|---|---|---|---|---|---|---|---|---|
| 5; 9; 9 | 6; 2; 1 | 6; 2; 2 | 6; 2; 3 | 6; 2; 4 | 6; 2; 5 | 6; 2; 6 | 6; 2; 7 | 6; 2; 8 | 6; 2; 9 | 6; 3; 1 | 6; 3; 2 |
| 6; 3; 3 | 6; 3; 4 | 6; 3; 5 | 6; 3; 6 | 6; 3; 7 | 6; 3; 8 | 6; 3; 9 | 6; 4; 1 | 6; 4; 2 | 6; 4; 3 | 6; 4; 4 | 6; 4; 5 |
| 6; 4; 6 | 6; 4; 7 | 6; 4; 8 | 6; 4; 9 | 6; 5; 1 | 6; 5; 2 | 6; 5; 3 | 6; 5; 4 | 6; 5; 5 | 6; 5; 6 | 6; 5; 7 | 6; 5; 8 |
| 6; 5; 9 | 6; 6; 1 | 6; 6; 2 | 6; 6; 3 | 6; 6; 4 | 6; 6; 5 | 6; 6; 6 | 6; 6; 7 | 6; 6; 8 | 6; 6; 9 | 6; 7; 1 | 6; 7; 2 |
| 6; 7; 3 | 6; 7; 4 | 6; 7; 5 | 6; 7; 6 | 6; 7; 7 | 6; 7; 8 | 6; 7; 9 | 6; 8; 1 | 6; 8; 2 | 6; 8; 3 | 6; 8; 4 | 6; 8; 5 |
| 6; 8; 6 | 6; 8; 7 | 6; 8; 8 | 6; 8; 9 | 6; 9; 1 | 6; 9; 2 | 6; 9; 3 | 6; 9; 4 | 6; 9; 5 | 6; 9; 6 | 6; 9; 7 | 6; 9; 8 |
| 6; 9; 9 | 7; 2; 1 | 7; 2; 2 | 7; 2; 3 | 7; 2; 4 | 7; 2; 5 | 7; 2; 6 | 7; 2; 7 | 7; 2; 8 | 7; 2; 9 | 7; 3; 1 | 7; 3; 2 |
| 7; 3; 3 | 7; 3; 4 | 7; 3; 5 | 7; 3; 6 | 7; 3; 7 | 7; 3; 8 | 7; 3; 9 | 7; 4; 1 | 7; 4; 2 | 7; 4; 3 | 7; 4; 4 | 7; 4; 5 |
| 7; 4; 6 | 7; 4; 7 | 7; 4; 8 | 7; 4; 9 | 7; 5; 1 | 7; 5; 2 | 7; 5; 3 | 7; 5; 4 | 7; 5; 5 | 7; 5; 6 | 7; 5; 7 | 7; 5; 8 |
| 7; 5; 9 | 7; 6; 1 | 7; 6; 2 | 7; 6; 3 | 7; 6; 4 | 7; 6; 5 | 7; 6; 6 | 7; 6; 7 | 7; 6; 8 | 7; 6; 9 | 7; 7; 1 | 7; 7; 2 |
| 7; 7; 3 | 7; 7; 4 | 7; 7; 5 | 7; 7; 6 | 7; 7; 7 | 7; 7; 8 | 7; 7; 9 | 7; 8; 1 | 7; 8; 2 | 7; 8; 3 | 7; 8; 4 | 7; 8; 5 |
| 7; 8; 6 | 7; 8; 7 | 7; 8; 8 | 7; 8; 9 | 7; 9; 1 | 7; 9; 2 | 7; 9; 3 | 7; 9; 4 | 7; 9; 5 | 7; 9; 6 | 7; 9; 7 | 7; 9; 8 |
| 7; 9; 9 | 8; 2; 1 | 8; 2; 2 | 8; 2; 3 | 8; 2; 4 | 8; 2; 5 | 8; 2; 6 | 8; 2; 7 | 8; 2; 8 | 8; 2; 9 | 8; 3; 1 | 8; 3; 2 |
| 8; 3; 3 | 8; 3; 4 | 8; 3; 5 | 8; 3; 6 | 8; 3; 7 | 8; 3; 8 | 8; 3; 9 | 8; 4; 1 | 8; 4; 2 | 8; 4; 3 | 8; 4; 4 | 8; 4; 5 |
| 8; 4; 6 | 8; 4; 7 | 8; 4; 8 | 8; 4; 9 | 8; 5; 1 | 8; 5; 2 | 8; 5; 3 | 8; 5; 4 | 8; 5; 5 | 8; 5; 6 | 8; 5; 7 | 8; 5; 8 |
| 8; 5; 9 | 8; 6; 1 | 8; 6; 2 | 8; 6; 3 | 8; 6; 4 | 8; 6; 5 | 8; 6; 6 | 8; 6; 7 | 8; 6; 8 | 8; 6; 9 | 8; 7; 1 | 8; 7; 2 |
| 8; 7; 3 | 8; 7; 4 | 8; 7; 5 | 8; 7; 6 | 8; 7; 7 | 8; 7; 8 | 8; 7; 9 | 8; 8; 1 | 8; 8; 2 | 8; 8; 3 | 8; 8; 4 | 8; 8; 5 |
| 8; 8; 6 | 8; 8; 7 | 8; 8; 8 | 8; 8; 9 | 8; 9; 1 | 8; 9; 2 | 8; 9; 3 | 8; 9; 4 | 8; 9; 5 | 8; 9; 6 | 8; 9; 7 | 8; 9; 8 |
| 8; 9; 9 | 9; 2; 1 | 9; 2; 2 | 9; 2; 3 | 9; 2; 4 | 9; 2; 5 | 9; 2; 6 | 9; 2; 7 | 9; 2; 8 | 9; 2; 9 | 9; 3; 1 | 9; 3; 2 |
| 9; 3; 3 | 9; 3; 4 | 9; 3; 5 | 9; 3; 6 | 9; 3; 7 | 9; 3; 8 | 9; 3; 9 | 9; 4; 1 | 9; 4; 2 | 9; 4; 3 | 9; 4; 4 | 9; 4; 5 |
| 9; 4; 6 | 9; 4; 7 | 9; 4; 8 | 9; 4; 9 | 9; 5; 1 | 9; 5; 2 | 9; 5; 3 | 9; 5; 4 | 9; 5; 5 | 9; 5; 6 | 9; 5; 7 | 9; 5; 8 |
| 9; 5; 9 | 9; 6; 1 | 9; 6; 2 | 9; 6; 3 | 9; 6; 4 | 9; 6; 5 | 9; 6; 6 | 9; 6; 7 | 9; 6; 8 | 9; 6; 9 | 9; 7; 1 | 9; 7; 2 |
| 9; 7; 3 | 9; 7; 4 | 9; 7; 5 | 9; 7; 6 | 9; 7; 7 | 9; 7; 8 | 9; 7; 9 | 9; 8; 1 | 9; 8; 2 | 9; 8; 3 | 9; 8; 4 | 9; 8; 5 |
| 9; 8; 6 | 9; 8; 7 | 9; 8; 8 | 9; 8; 9 | 9; 9; 1 | 9; 9; 2 | 9; 9; 3 | 9; 9; 4 | 9; 9; 5 | 9; 9; 6 | 9; 9; 7 | 9; 9; 8 |
| 9; 9; 9. | | | | | | | | | | | |

For example, the structure of oligopeptide 1;1;1 is as follows:

```
PFPQPQLPY PFPQPQLPY PFPQPQLPY.     (SEQ ID NO: 26)
```

In the foregoing manner, each of the remaining oligopeptides listed above is described to the same extent as oligopeptide 1;1;1 has been described.

In a further embodiment, the oligopeptides of the present invention contain "flanking sequences," which herein refer to sequences comprising at least one amino acid at the amino terminus and/or carboxyl terminus of the oligopeptide that is not an epitope. As such, oligopeptides of the present invention can contain flanking sequences comprising one, two, three, four, or more amino acids at the amino terminus and/or at the carboxyl terminus, as long as the flanking sequences are not epitopes.

Other oligopeptides of the invention useful in the methods of the invention include oligopeptides having the following sequences, and fragments thereof: (SEQ ID NO:13) QPQPF-PPQLPYPQTQPFPPQQPYPQPQPQYPQPQ (from α1- and α6-gliadins); (SEQ ID NO:14) QQQPF-PQQPIPQQPQPYPQQPQPYPQQPFPPQQPF (from B1 hordein); (SEQ ID NO:15) QPFPQPQQTFPQQPQLPF-PQQPQQPFPQPQ; (SEQ ID NO:16) PQQPQLPF-PQQPQQPFPQPQQPQQPFPQSQQPQQPF-PQPQQQFPQPQQPQQSFPQQQQ P (from γ-gliadin); and (SEQ ID NO:17) QPFPQPQQPTPIQPQQPFPQRPQQPF-PQPQ. These oligopeptides are resistant toward endo- and exo-proteolysis by gastric, pancreatic and small intestinal enzymes, comprise multiple epitopes, and are recognized by tTGase. See, for example, Molberg et al, (1998) Nat. Med.; Vader et al, (2002) J. Exp. Med.; Sollid, et al. (2000) Ann. Rev. Immunol 2000; Vader et al, (2003) Gastroenterology; and Osman et al (2000) Clin. Exp. Immunol. 121, 248-254.

Antibodies may also recognize conformational determinants formed by non-contiguous residues on an antigen, and an epitope can therefore require a larger fragment of the antigen to be present for binding, e.g. a protein domain, or substantially all of a protein sequence. The binding site of antibodies typically utilizes multiple non-covalent interactions to achieve high affinity binding. While a few contact residues of the antigen may be brought into close proximity to the binding pocket, other parts of the antigen molecule can also be required for maintaining a conformation that permits binding. In order to consider an antibody interaction to be "specific", the affinity will be at least about $10^{-7}$ M, usually about $10^{-8}$ M to $10^{-9}$ M, and may be up to $10^{-11}$ M or higher for the epitope of interest. It will be understood by those of skill in the art that the term "specificity" refers to such a high affinity binding, and is not intended to mean that the antibody cannot bind to other molecules as well. One may find cross-reactivity with different epitopes, due, e.g. to a relatedness of antigen sequence or structure, or to the structure of the antibody binding pocket itself.

The T cell receptor recognizes a more complex structure than antibodies, and requires both a major histocompatibility antigen binding pocket and an antigenic peptide to be present. The binding affinity of T cell receptors is lower than that of antibodies, and will usually be at least about $10^{-4}$ M, more usually at least about $10^{-5}$ M.

Affinity and stability are different measures of binding interaction. The definition of affinity is a thermodynamic expression of the strength of interaction between a single antigen binding site and a single antigenic determinant (and thus of the stereochemical compatibility between them). Affinity does not change with valency, because it is the measure of interaction between a single binding site and a single antigenic determinant. In contrast to affinity, avidity (which relates to the $t_{1/2}$ of an interaction) is defined as the strength of binding, usually of a small molecule with multiple binding sites by a larger molecule, and in particular, the binding of a complex antigen by an antibody. Therefore, it is avidity that takes into account the effect of multiple interactions, and it is the change in avidity that may provides the hyperantigenicity observed with the oligopeptide of SEQ ID NO:12.

It is also shown herein that the 33-mer (SEQ ID NO:12) is a particularly good substrate for the enzyme tTGase, which deamidates the 33-mer at least at the underlined positions shown in the following sequence: (SEQ ID NO:12) LQLQPFPQPQLPYPQPQLPYPQPQLPYPQPQPF.

Antigenic oligopeptides of the present invention may comprise deamidated glutamine residues at one, two, three or more positions, which positions may or may not correspond with those of the naturally deamidated oligopeptides.

The 33-mer (SEQ ID NO:12) and its deamidated counterparts have been tested for an ability to stimulate monoclonal and polyclonal T cell lines from Celiac Sprue individuals. Their stimulatory ability was compared with that of a number of immunogenic epitopes contained in shorter peptides, and the 33-mer and its deamidated counterparts were shown to be far more specific and potent than the shorter peptides.

These results provide the basis for a number of improved diagnostic methods for Celiac Sprue as well as a variety of reagents useful in those and other methods. The multivalent gluten oligopeptides described herein, including those comprising SEQ ID NO:12; deamidated counterparts, derivatives, analogs, and conservatively modified variants thereof, are useful in stimulating T cells from Celiac Sprue patients for diagnostic purposes, and so are provided by the present invention in isolated and highly purified forms. Further, the multivalent gluten oligopeptides described herein, including those comprising SEQ ID NO:12; deamidated counterparts, derivatives, analogs, and conservatively modified variants thereof, are useful in diagnostic assays for detecting antibodies against such oligopeptides or for producing antibodies that bind specifically to such oligopeptides for their detection.

Transglutaminase Oligopeptide Fusions

In one embodiment of the invention, a fusion protein comprising all or a portion of a mammalian tTGase, including but not limited to human, bovine, equine, and porcine tTGase, is linked, usually covalently, to a multivalent gluten oligopeptide of the invention, wherein the linkage site is at a site for eventual deamidation. This fusion protein of the invention is a highly potent stimulator of T cells from Celiac Sprue patients in that the fusion protein exactly mimics the complexes formed in Celiac Sprue patients and is recognized by the anti-tTGase antibodies and by T cells in those patients. Such fusion proteins find use in the diagnostic methods of the invention.

Transglutaminases (EC 2.3.2.13) are a family of enzymes that catalyze the crosslinking of proteins by epsilon-gamma glutamyl lysine isopeptide bonds. The human haploid genome contains at least 8 distinct transglutaminases that are differentially expressed in time-space and tissue-specific ways, and these enzymes find use in the present invention. Although the overall primary structures of these enzymes appear to be quite different, they all share a common amino acid sequence at the active site (Y-G-Q-C-W) and a strict calcium dependence for their activity. The differences in the primary structures of these different transglutaminases are responsible for the diverse biologic functions that they play in physiologic processes.

Transglutaminases of particular interest include the human TG1, TG2 and TG3 enzymes. Keratinocyte transglutaminase, TG1, has the Genbank accession number D90287 (see Phillips et al. (1990) Proc. Natl. Acad. Sci. U.S.A. 87(23):9333-9337; Yamanishi et al. (1991) Biochem. Biophys. Res. Commun. 175(3):906-913). It is normally expressed in skin, and is involved in the barrier formation of keratinocytes. The human protein has a molecular mass of about 90 kD, having a 105-residue extension beyond the N terminus of the tissue transglutaminase (TG2). The deduced 813-amino acid sequence of the TG1 protein shares 49 to 53% homology with other transglutaminase proteins of known sequence.

Tissue transglutaminase 2 (TG2) has the Genbank accession number M55153, and encodes a 687 amino acid protein. It is expressed as a 3.6 kb mRNA in human endothelial cells. Tissue transglutaminase 3 (TG3) has the Genbank accession number L10386, and encodes a 692 amino acid protein. It is expressed as a 2.9-kb mRNA. The sequences of TG2 and TG3 find use in the recombinant production of the encoded polypeptide.

Transglutaminase polypeptides can be produced through isolation from natural sources, recombinant methods and chemical synthesis. In addition, functionally equivalent polypeptides may find use, where the equivalent polypeptide may contain deletions, additions or substitutions of amino acid residues that result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved. "Functionally equivalent", as used herein, refers to a protein capable of exhibiting a substantially similar activity as the native polypeptide.

The polypeptides may be produced by recombinant DNA technology using techniques well known in the art. Methods that are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized.

As described in the examples, during normal digestion, a peptidase resistant oligopeptide core remains after exposure of glutens, e.g. gliadin, to normal digestive enzymes. Oligopeptide fragments of interest include fragments of at least about 20 contiguous amino acids, more usually at least about 33 contiguous amino acids, and may comprise 50 or more amino acids, and may extend further to comprise additional sequences. Examples of other peptidase resistant oligopeptides are provided in SEQ ID NO:5, 6, 7 and 10. Other examples of immunogenic gliadin oligopeptides are discussed by Wieser (1995) Baillieres Clin Gastroenterol 9(2): 191-207.

The multivalent gluten oligopeptides may be substituted with a glutamine analog at one or more positions, e.g. to enhance formation of a complex or covalent binding between tTGase and the peptid analog. Analogs useful in the preparation of substituted peptide for this purpose include the following:

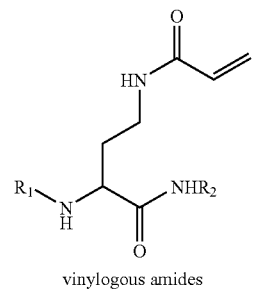

vinylogous amides

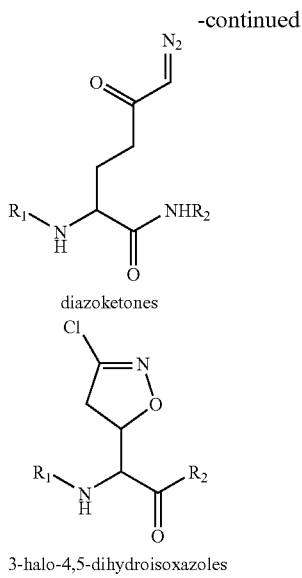

diazoketones 3-halo-4,5-dihydroisoxazoles where R1 and R2 are independently selected from H, alkyl, alkenyl, cycloalkyl, aryl, heteroalkyl, heteroaryl, alkoxy, alkylthio, arakyl, aralkenyl, halo, haloalkyl, haloalkoxy, heterocyclyl, and heterocyclylalkyl groups. R1 and R2 may also comprise peptidic protecting groups. The amino acid analogs, 6-diazo-5-oxo-norleucine (Don), Azaserine (Aza), 6-thio(tetramethyl imidazoyl)-5-oxo-norleucine (Ton), 2-[2-thio(tetramethyl imidazoyl)-acyl]-2,3-diaminopropionic acid (Tad), acivicin (Aci)) and 3-chloro-4,5-dihydro-5-amino-isoxazole are also proposed as glutamine mimetics.

Polypeptide and Oligopeptide Compositions

The oligopeptides and proteins useful in the methods of the present invention may be prepared in accordance with conventional techniques, such as synthesis, recombinant techniques, isolation from natural sources, or the like. For example, solid-phase peptide synthesis involves the successive addition of amino acids to create a linear peptide chain (see Merrifield (1963) J. Am. Chem. Soc. 85:2149-2154). Production of a peptide or protein by recombinant DNA technology can also be performed. Thus, the oligopeptides may be prepared by in vitro synthesis, using conventional methods as known in the art. Various commercial synthetic apparatuses are available, for example, automated synthesizers by Applied Biosystems, Inc., Foster City, Calif., Beckman, and other manufacturers. By using synthesizers, naturally occurring amino acids may be substituted with unnatural amino acids. The particular sequence and the manner of preparation will be determined by convenience, economics, purity required, and the like.

The sequence of the provided epitopes, and of amino acids flanking epitopes, may be altered in various ways known in the art to generate targeted changes in sequence. Such "conservatively modified variants" will typically be functionally-preserved variants, which differ, usually in sequence, from the corresponding native or parent oligopeptide but still retain the biological activity, i.e., epitopic specificity. Variants may also include fragments of the oligopeptide that retain activity. Various methods known in the art may be used to generate targeted changes, e.g. phage display in combination with random and targeted mutations, introduction of scanning mutations, and the like.

A variant may be substantially similar to a native sequence, i.e. differing by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of proteins, e.g., acetylation, or carboxylation. Also included in the subject invention are oligopeptides that have been modified using molecular biological techniques and synthetic chemistry so as to improve their resistance to proteolytic degradation, to acidic conditions such as those found in the stomach, or to optimize solubility properties or to render them more suitable as a therapeutic agent. For examples, the backbone of the peptidase may be cyclized to enhance stability (see Friedler et al. (2000) J. Biol. Chem. 275:23783-23789). Analogs of such proteins include those containing residues other than naturally occurring L-amino acids, e.g. D-amino acids or non-naturally occurring synthetic amino acids. If desired, various groups may be introduced into the oligopeptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Thus, the present invention includes oligopeptide analogs of the oligopeptides described by amino acid sequence herein. Such analogs contain at least one difference in amino acid sequence between the analog and native antigenic peptide. An L-amino acid from the native peptide may be altered to any other one of the 20 L-amino acids commonly found in proteins, any one of the corresponding D-amino acids, rare amino acids, such as 4-hydroxyproline, and hydroxylysine, or a non-protein amino acid, such as β-alanine and homoserine. Also included with the scope of the present invention are amino acids that have been altered by chemical means such as methylation (e.g., α-methylvaline), deamidation, amidation of the C-terminal amino acid by an alkylamine such as ethylamine, ethanolamine, and ethylene diamine, and acylation or methylation of an amino acid side chain function (e.g., acylation of the epsilon amino group of lysine), deimination of arginine to citrulline, isoaspartylation, or phosphorylation on serine, threonine, tyrosine or histidine residues. Candidate oligopeptide analogs may be screened for utility in a diagnostic method of the invention by an assay measuring competitive binding to MHC, and an assay measuring T cell proliferation. Those analogs that inhibit binding of the native peptides and that stimulate proliferation of autoreactive T cells are useful diagnostic reagents.

Oligopeptides and oligopeptide analogs may be synthesized by standard chemistry techniques, including synthesis by automated procedure. In general, peptide and peptide analogs are prepared by solid-phase peptide synthesis methodology which involves coupling each protected amino acid residue to a resin support, preferably a 4-methylbenzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminus. After the last residue has been attached, the protected peptide-resin is treated with hydrogen fluoride to cleave the peptide from the resin, as well as deprotect the side chain functional groups. Crude product can be further purified by gel filtration, HPLC, partition chromatography, or ion-exchange chromatography.

The oligopeptides may also be isolated and purified in accordance with conventional methods of recombinant synthesis, or from natural sources. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for diagnostic purposes, usually at least about 99.5% by weight, in relation to contaminants related to the method of preparation of the product and its purification. Usually, the percentages will be based upon total protein.

The peptides and proteins of the invention can also be used to generate other useful reagents of the invention, including monoclonal and polyclonal antibody-producing cell lines and antibodies derived therefrom in isolated and purified form. The peptides and proteins of the invention can also be used to generate highly purified preparations of T cell lines, the proliferation of which is stimulated by those peptides and proteins. Such cell lines and antibodies are useful in diagnostic methods of the invention.

Diagnostic Methods

The present invention provides a variety of methods for diagnosing Celiac Sprue. In one embodiment, the diagnosis involves detecting the presence of a gluten oligopeptides digestion product, e.g. SEQ ID NO:12; deamidated counterparts there; a tTGase-linked counterpart thereof; etc., in a tissue, bodily fluid, or stool of an individual. The detecting step can be accomplished by use of a reagent, e.g. an antibody, that recognizes the indicated antigen, or by a cell that proliferates in the presence of the indicated antigen and suitable antigen presenting cells, wherein said antigen presenting cells are compatible with the MHC type of the proliferating cell, e.g. allogeneic cells, autologous cells, etc.

In another embodiment, the diagnosis involves detecting the presence of an antibody, one or more T cells reactive with the 33-mer or a deamidated counterpart thereof, or a tTGase-linked counterpart thereof in a tissue, bodily fluid, or stool of an individual. In one embodiment, an antibody is detected by, for example, an agglutination assay using an antigen provided by the present invention. In another embodiment, a T cell is detected by its proliferation in response to exposure to a multivalent gluten oligopeptide provided by the present invention and presented by autologous or suitable allogeneic antigen presenting cells.

In one aspect, the methods and reagents of the present invention are capable of detecting the toxic oligopeptides of gluten proteins of wheat, barley, oats and rye remaining after digestion or partial digestion of the same by a Celiac Sprue individual. Gluten is the protein fraction in cereal dough, which can be subdivided into glutenins and prolamines, which can be further subclassified as gliadins, secalins, hordeins, avenins from wheat, rye, barley and oat, respectively. For further discussion of gluten proteins, see the review by Wieser (1996) Acta Paediatr Suppl. 412:3-9; herein incorporated by reference. Among gluten proteins of interest are included the storage proteins of wheat, species of which include *Triticum aestivum; Triticum aethiopicum; Triticum baeoticum; Triticum militinae; Triticum monococcum; Triticum sinskajae; Triticum timopheevii; Tnticum turgidum; Triticum urartu, Triticum vavilovii; Triticum zhukovskyi*; and the like. A review of the genes encoding wheat storage proteins may be found in Colot (1990) *Genet Eng* (N Y) 12:22541.

Of particular interest is gliadin, which is the alcohol-soluble protein fraction of wheat gluten. Gliadins are typically rich in glutamine and proline, particularly in the N-terminal part. For example, the first 100 amino acids of α- and γ-gliadins contain ~35% and ~20% of glutamine and proline residues, respectively. Many wheat gliadins have been characterized, and as there are many strains of wheat and other cereals, it is anticipated that many more sequences will be obtained using routine methods of molecular biology. Examples of sequenced gliadins include wheat alpha gliadin sequences, for example as provided in Genbank, accession numbers AJ133612; AJ133611; AJ133610; AJ133609; AJ133608; AJ133607; AJ133606; AJ133605; AJ133604; AJ133603; AJ133602; D84341.1; U51307; U51306; U51304; U51303; U50984; and U08287. A sequence of wheat omega gliadin is set forth in Genbank accession number AF280605.

For the purposes of the present invention, toxic gliadin oligopeptides are peptides derived during normal digestion of gliadins and related storage proteins as described above, from dietary cereals, e.g. wheat, rye, barley, and the like, by a Celiac Sprue individual. Such oligopeptides are believed to act as antigens for T cells in Celiac Sprue individuals. For binding to Class II MHC proteins, immunogenic peptides are usually from about 6 to 20 amino acids in length, more usually from about 10 to 18 amino acids, and as demonstrated herein, a particularly stimulatory toxic gliadin oligopeptide is the multivalent 33-mer described above. Such peptides include PXP motifs, for example the motif PQPQLP (SEQ ID NO:8). Determination of whether an oligopeptide is immunogenic for a particular patient is readily determined by standard T cell activation assays known to those of skill in the art. Illustrative toxic gliadin oligopeptides of the invention are described in Examples 1 and 2 below. The 33-mer gliadin oligopeptide of Example 2 and its deamidated counterpart formed by tTGase are preferred toxic gliadin oligopeptides of the invention.

Samples may be obtained from patient tissue, which may be a mucosal tissue, including but not limited to oral, nasal, lung, and intestinal mucosal tissue, a bodily fluid, e.g. blood, sputum, urine, phlegm, lymph, and tears. One advantage of the present invention is that the antigens provided are such potent antigens, both for antibody-binding and T-cell stimulation, that the diagnostic methods of the invention can be employed with samples (tissue, bodily fluid, or stool) in which a Celiac Sprue diagnostic antibody, peptide, or T cell is present in very low abundance. This allows the methods of the invention to be practiced in ways that are much less invasive, much less expensive, and much less harmful to the Celiac Sprue individual.

Patients may be monitored for the presence of reactive T cells, using one or more multivalent oligopeptides as described above. The presence of such reactive T cells indicates the presence of an on-going immune response. The antigen used in the assays is a multivalent gluten oligopeptide as described above; including, without limitation, SEQ ID NO:12; deamidated counterparts; tTGase fusions thereof; and derivatives. Cocktails comprising multiple oligopeptides; panels of peptides; etc. may be also used. Overlapping peptides may be generated, where each peptide is frameshifted from 1 to 5 amino acids, thereby generating a set of epitopes.

The diagnosis may determine the level of reactivity, e.g. based on the number of reactive T cells found in a sample, as compared to a negative control from a naive host, or standardized to a data curve obtained from one or more positive controls. In addition to detecting the qualitative and quantitative presence of antigen reactive T cells, the T cells may be typed as to the expression of cytokines known to increase or suppress inflammatory responses. While not necessary for diagnostic purposes, it may also be desirable to type the epitopic specificity of the reactive T cells, particularly for use in therapeutic administration of peptides.

T cells may be isolated from patient peripheral blood, lymph nodes, including peyer's patches and other gut-related lymph nodes, or from tissue samples as described above. Reactivity assays may be performed on primary T cells, or the cells may be fused to generate hybridomas. Such reactive T cells may also be used for further analysis of disease progression, by monitoring their in situ location, T cell receptor utilization, MHC cross-reactivity, etc. Assays for monitoring T cell responsiveness are known in the art, and include proliferation assays and cytokine release assays. Also of interest is an ELISA spot assay.

Proliferation assays measure the level of T cell proliferation in response to a specific antigen, and are widely used in the art. In one such assay, recipient lymph node, blood or spleen cells are obtained at one or more time points after transplantation. A suspension of from about $10^4$ to $10^7$ cells, usually from about $10^5$ to $10^6$ cells is prepared and washed, then cultured in the presence of a control antigen, and test antigens, as described above. The cells are usually cultured for several days. Antigen-induced proliferation is assessed by the monitoring the synthesis of DNA by the cultures, e.g. incorporation of $^3$H-thymidine during the last 18 H of culture.

T cell cytotoxic assays measure the numbers of cytotoxic T cells having specificity for the test antigen. Lymphocytes are obtained at different time points after transplantation. Alloreactive cytotoxic T cells are tested for their ability to kill target cells bearing recipient MHC class I molecules associated with peptides derived from a test antigen. In an exemplary assay, target cells presenting peptides from the test antigen, or a control antigen, are labeled with $Na^{51}CrO_4$. The target cells are then added to a suspension of candidate reactive lymphocytes. The cytotoxicity is measured by quantitating the release of $Na^{51}CrO_4$ from lysed cells. Controls for spontaneous and total release are typically included in the assay. Percent specific $^{51}Cr$ release may be calculated as follows: 100× (release by CTL−spontaneous release)/(total release− spontaneous release).

Enzyme linked immunosorbent assay (ELISA) and ELISA spot assays are used to determine the cytokine profile of reactive T cells, and may be used to monitor for the expression of such cytokines as IL-2, IL4, IL-5, γIFN, etc. The capture antibodies may be any antibody specific for a cytokine of interest, where supernatants from the T cell proliferation assays, as described above, are conveniently used as a source of antigen. After blocking and washing, labeled detector antibodies are added, and the concentrations of protein present determined as a function of the label that is bound.

In one embodiment of the invention, the presence of reactive T cells is determined by injecting a dose of the 33-mer peptide, or a derivative or fragment thereof as described above, subcutaneously or sub-mucosally into a patient, for example into the oral mucosa (see Lahteenoja et al. (2000) Am. J. Gastroenterology 95:2880, herein incorporated by reference). A control comprising medium alone, or an unrelated protein is usually injected nearby at the same time. The site of injection is examined after a period of time, by biopsy or for the presence of a wheal.

A wheal at the site of injection is compared to that at the site of the control injection, usually by measuring the size of the wheal. The skin test readings may be assessed by a variety of objective grading systems. A positive result for the presence of an immune response will show an increased diameter at the site of polypeptide injection as compared to the control.

Where a biopsy is performed, the specimen is examined for the presence of increased numbers of immunologically active cells, e.g. T cells, B cells, mast cells, and the like. For example, methods of histochemistry and/or immunohistochemistry may be used, as is known in the art. The densities of cells, including antigen specific T cells, mast cells, B cells, etc. may be examined. It has been reported that increased numbers of intraepithelial CD8+T cells may correlate with gliadin reactivity.

An alternative method relies on the detection of circulating antibodies in a patient. Methods of detecting specific antibodies are well-known in the art. Antibodies specific for multivalent gluten oligopeptides as described above may be used in screening immunoassays. A sample is taken from the patient. Samples, as used herein, include biological fluids such as blood, tears, saliva, lymph, dialysis fluid and the like; organ or tissue culture derived fluids; and fluids extracted from physiological tissues. Also included in the term are derivatives and fractions of such fluids. Blood samples and derivatives thereof are of particular interest.

Measuring the concentration of specific antibodies in a sample or fraction thereof may be accomplished by a variety of specific assays. In general, the assay will measure the reactivity between a patient sample, usually blood derived, generally in the form of plasma or serum. The patient sample may be used directly, or diluted as appropriate, usually about 1:10 and usually not more than about 1:10,000. Immunoassays may be performed in any physiological buffer, e.g. PBS, normal saline, HBSS, dPBS, etc.

In one embodiment, a conventional sandwich type assay is used. A sandwich assay is performed by first attaching the peptide to an insoluble surface or support. The peptide may be bound to the surface by any convenient means, depending upon the nature of the surface, either directly or through specific antibodies. The particular manner of binding is not crucial so iong as it is compatible with the reagents and overall methods of the invention. They may be bound to the plates covalently or non-covalently, preferably non-covalently.

The insoluble supports may be any composition to which peptides can be bound, which is readily separated from soluble material, and which is otherwise compatible with the overail method of measuring antibodies. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Before adding patient samples or fractions thereof, the non-specific binding sites on the insoluble support i.e. those not occupied by antigen, are generally blocked. Preferred blocking agents include non-interfering proteins such as bovine serum albumin, casein, gelatin, and the like. Alternatively, several detergents at non-interf ring concentrations, such as Tween, NP40, TX100, and the like may be used.

Samples, fractions or aliquots thereof are then added to separately assayable supports (for example, separate wells of a microtiter plate) containing support-bound antigenic peptide. Preferably, a series of standards, containing known concentrations of antibodies is assayed in parallel with the samples or aliquots thereof to serve as controls.

Generally from about 0.001 to 1 ml of sample, diluted or otherwise, is sufficient, usually about 0.01 ml sufficing. Preferably, each sample and standard will be added to multiple wells so that mean values can be obtained for each. The incubation time should be sufficient for antibodies molecules to bind the insoluble antigenic peptide. Generally, from about 0.1 to 3 hr is sufficient, usually 1 hr sufficing.

After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash non-specifically bound proteins present in the sample.

After washing, a solution containing a second receptor specific for the patient antibodies is applied. The receptor may be any compound that binds patient antibodies with sufficient specificity such that it can be distinguished from other components present. In a preferred embodiment, second receptors are antibodies specific for patient antibodies, either monoclonal or polyclonal sera, e.g. mouse anti-human antibodies, mouse anti-dog antibodies, rabbit anti-cat antibodies, etc. Such second stage antibodies may be labeled to facilitate direct, or indirect quantification of binding. Examples of labels which permit direct measurement of second receptor binding include radiolabels, such as $^3$H or $^{125}$I, fluorescers, dyes, beads, chemilumninescers, colloidal particles, and the like. Examples of labels that permit indirect measurement of binding include enzymes where the substrate may provide for a colored or fluorescent product. In a preferred embodiment, the second receptors are antibodies labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Alternatively, the second stage may be unlabeled, and a labeled third stage is used. Examples of second receptor/second receptor-specific molecule pairs include antibody/anti-antibody and avidin (or streptavidin)/biotin. Since the resultant signal is thus amplified, this technique may be advantageous where only a small amount of antibodies is present.

After the second stage has bound, the insoluble support is generally again washed free of non-specifically bound molecules, and the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and is O-phenylenediamine, which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490495 nm is conveniently measured with a spectrophotometer.

Generally the amount of bound antibodies detected will be compared to control samples from normal patients. The presence of increased levels of the antigen specific antibodies is indicative of disease, usually at least about a 5 fold, 10 fold, or 100 fold increase will be taken as a positive reaction.

In some cases, a competitive assay will be used. In addition to the patient sample, a competitor to the antibodies is added to the reaction mix. The competitor and the antibodies compete for binding to the antigenic peptide. Usually, the competitor molecule will be labeled and detected as previously described, where the amount of competitor binding will be proportional to the amount of antibodies present. The concentration of competitor molecule will be from about 10 times the maximum anticipated antibodies concentration to about equal concentration in order to make the most sensitive and linear range of detection.

An alternative protocol is to provide anti-patient antibodies bound to the insoluble surface. After adding the sample and washing away non-specifically bound proteins, one or a combination of the test antigens are added, where the antigens are labeled, so as not to interfere with binding to the antibodies. Conveniently, fused proteins may be employed, where the peptide sequence is fused to an enzyme sequence, e.g. β-galactosidase.

It is particularly convenient in a clinical setting to perform the immunoassay in a self-contained apparatus. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it the antigenic peptide, with a conjugate of an enzyme with an antibodies specific antibody employed as a reagent, generally added to the sample before application. Alternatively, the antigenic peptide may be conjugated to an enzyme, with antibodies specific antibody bound to the measurement region.

Thus, in one aspect, the present invention provides a method for diagnosing Celiac Sprue in an individual who has not consumed gluten for an extended period of time, such time including but not limited to one day, one week, one month, and one year prior to the performance of the diagnostic method. The advantage conferred by this aspect of the invention is that current diagnosis of a Celiac Sprue individual typically involves a preliminary diagnosis, after which the individual is placed on a gluten-free diet. If the individual's symptoms abate after initiation of the gluten-free diet, then the individual is challenged with gluten, and another diagnostic test, such as an endoscopy or T cell proliferation assay, is performed to confirm the preliminary diagnosis. This re-challenge with gluten causes extreme discomfort to the Celiac Sprue individual. One important benefit provided by certain embodiments of the invention is that such a re-challenge need not be performed to diagnose Celiac Sprue, because even very low levels of 33-mer specific antibodies and T cell responders can be identified using the methods of the invention.

In another aspect, the present invention provides a method for diagnosing Celiac Sprue by detecting the presence of a 33-mer specific antibody or a T cell responder in a bodily tissue or fluid other than intestinal mucosa. In this aspect of the invention, the diagnostic methods are performed without recourse to endoscopy or intestinal biopsy, thus avoiding the discomfort, pain, and expense attendant on such procedures in common use today.

The subject methods are useful not only for diagnosing Celiac Sprue individuals but also for determining the efficacy of prophylactic or therapeutic methods for Celiac Sprue as well as the efficacy of food preparation or treatment methods aimed at removing glutens or similar substances from food sources. Thus, a Celiac Sprue individual efficaciously treated with a prophylactic or therapeutic drug or other therapy for Celiac Sprue tests more like a non-Celiac Sprue individual with the methods of the invention. Likewise, the antibodies or T cell responders, e.g. T cell lines, of the invention that detect the toxic gluten oligopeptides of the invention are useful in detecting gluten and gluten-like substances in food and so can be used to determine whether a food treated to remove such substances has been efficaciously treated.

As used herein, the term "treating" is used to refer to both prevention of disease, and treatment of pre-existing conditions. The treatment of ongoing disease, to stabilize or improve the clinical symptoms of the patient, is of particular interest. Such treatment is desirably performed prior to loss of function in the affected tissues. Evidence of therapeutic effect may be any diminution in the severity of disease, particularly measuring the severity of such symptoms as fatigue, chronic diarrhea, malabsorption of nutrients, weight loss, abdominal distension, and anemia. Other disease indicia include the presence of antibodies specific for the 33-mer of the invention or its deamidated counterparts, glutens, antibodies specific for tissue transglutaminase or tTGase link d to the 33-mer of the invention or its deamidated counterparts, the presence of pro-inflammatory T cells and cytokines, histological examination of the villus structure of the small intestine, and the like. Patients may be adult or child, where children in particular benefit from prophylactic treatment, as prevention of early exposure to toxic gluten peptides may prevent initial development of the disease. Children suitable for prophylaxis can be identified by genetic testing for predisposition, e.g. by HLA typing; by family history, and, preferably, by the diagnostic methods of the present invention.

Although the present invention is not to be bound by any theory of action of the glutenases, it is believed that the primary event in Celiac Sprue requires intact gluten oligopeptides such as the 33-mer of the invention to gain access to antigen binding sites within the lamina propria region interior to the relatively impermeable surface intestinal epithelial layer. Ordinarily, oligopeptide end products of pancreatic protease processing are rapidly and efficiently hydrolyzed into amino acids, di- or tri-peptides by gastric peptidases before they can be transported across the epithelial layer. However, glutens have been found to be particularly peptidase resistant, which may be attributed to the usually high proline content of these proteins, a residue that is inaccessible to most gastric peptidases.

The normal assimilation of dietary proteins by the human gut can be dissected into three major phases: (i) initiation of proteolysis in the stomach by pepsin and highly efficient endo- and C-terminal cleavage in the upper small intestine cavity (duodenum) by secreted pancreatic proteases and carboxypeptidases; (ii) further processing of the resulting oligopeptide fragments by exo- and endopeptidases anchored in the brush border surface membrane of the upper small intestinal epithelium aejunum); and (iii) facilitated transport of the resulting amino acids, di- and tripeptides across the epithelial cells into the lamina propria, from where these nutrients enter capillaries for distribution throughout the body. Because most proteases and peptidases are unable to hydrolyze the amide bonds of proline residues, it is shown herein that the abundance of proline residues in gliadins and related proteins from wheat, rye and barley can constitute a major digestive obstacle for the enzymes involved in phases (i) and (ii) above. This leads to an increased concentration of relatively stable gluten derived oligopeptides in the gut.

Tissue transglutaminase (tTGase), an enzyme found on the extracellular surface in many organs including the intestine, catalyzes the formation of isopeptide bonds between glutamine and lysine residues of different polypeptides, leading to protein-protein crosslinks in the extracellular matrix. The tTGase enzyme is the primary focus of the autoantibody response in Celiac Sprue. Gliadins, secalins and hordeins contain several sequences rich in Pro-Gln residues that are high-affinity substrates for tTGase; tTGase catalyzed deamidation of at least some of these sequences, such as, in particular, the 33-mer oligopeptide of the invention, dramatically increases their affinity for HLA-DQ2, the class II MHC allele present in >90% Celiac Sprue patients; and presentation of these deamidated epitopes by DQ2 positive antigen presenting cells effectively stimulates proliferation of gliadin-specific T cells from intestinal biopsies of most Celiac Sprue patients. Proposed toxic effects of gluten include immunogenicity of the gluten oligopeptides, leading to inflammation, including by a mechanism in which gliadin peptides directly bind to surface receptors.

The various methods and reagents of the invention can be prepared and modified as described below. Although specific methods and reagents are exemplified in the discussion below, it is understood that any of a number of alternative methods, including those described above are equally applicable and suitable for use in practicing the invention. It will also be understood that an evaluation of the methods of the invention may be carried out using procedures standard in the art, including the diagnostic and assessment methods described above.

The practice of the present invention may employ conventional techniques of molecular biology (including recombinant techniques), microbiology, cell biology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction" (Mullis et al., eds., 1994); and "Current Protocols in Immunology" (J. E. Coligan et al., eds., 1991).

As noted above, the subject methods are useful to monitor the progress and efficacy of therapies to treat individuals suffering from Celiac Sprue and/or dermatitis herpetiformis. Such therapies can involve administration of an effective dose of glutenase and/or tTGase inhibitor, through a pharmaceutical formulation, incorporating glutenase into food products, administering live organisms that express glutenase, and the like. As these therapies may not have been approved by the FDA or an equivalent other regulatory agency, the methods of the invention have application in clinical trials conducted to evaluate the safety and efficacy of such therapies. Diagnosis of suitable patients may utilize a variety of criteria known to those of skill in the art in addition to those methods described herein. A quantitative increase in antibodies specific for gliadin, and/or tissue transglutaminase is indicative of the disease. Family histories and the presence of the HLA alleles HLA-DQ2 [DQ(a1*0501, b1*02)] and/or DQ8 [DQ (a1*0301, b1*0302)] are indicative of a susceptibility to the disease.

In addition to employing the diagnostic methods of the invention, the therapeutic effect may be measured in terms of clinical outcome, or may rely on immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Alternatively, one may look for a reduction in symptoms of a disease.

Related applications include U.S. Provisional application No. 60/357,238 filed Feb. 14, 2002; to U.S. Provisional Application No. 60/380,761 filed May 14, 2002; to U.S. Provisional Application No. 60/392,782 filed Jun. 28, 2002; and U.S. Provisional application No. 60/422,933, filed Oct. 31, 2002, each of which are herein specifically incorporated by reference.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Immunodominant Peptides of Gliadin are Protease Resistant

Recent studies have identified a small number of immunodominant peptides from gliadin, which account for most of the stimulatory activity of dietary gluten on intestinal and peripheral T lymphocytes found in Celiac patients. The proteolytic kinetics of these immunodominant peptides were analyzed at the small intestinal surface. Using brush border membrane vesicles from adult rat intestines, it was shown that these proline-glutamine-rich peptides are exceptionally resistant to enzymatic processing, and that dipeptidyl peptidase IV and dipeptidyl carboxypeptidase are the rate-limiting enzymes in their digestion. These results support the conclusions drawn from the tests described in Example 2 that incomplete digestion of gliadin, which results in the formation of the 33-mer oligopeptide and its deamidated counterpart formed by tTGase action, contributes to the disease symptoms of Celiac Sprue and can be employed in improved diagnostic methods for Celiac Sprue.

To dissect this complex process, liquid chromatography coupled mass spectroscopy analysis (LC-MS-MS) was utilized to investigate the pathways and associated kinetics of hydrolysis of immunodominant gliadin peptides treated with rat BBM preparations. Because the rodent is an excellent small animal model for human intestinal structure and function, rat BBM was chosen as a suitable model system for these studies.

BBM fractions were prepared from rat small intestinal mucosa as described by Ahnen et al. (1982) *J. Biol. Chem.* 257, 12129-35. Using standard assays, the specific activities of the known BB peptidases were determined to be 127 µU/µg for Aminopeptidase N (APN, EC 3.4.11.2), 60 µU/µg for dipeptidyl peptidase IV (DPP IV, EC 3.4.14.5), and 41 µU/µg for dipeptidyl carboxypeptidase (DCP, EC 3.4.15.1). No proline aminopeptidase (EC 3.4.11.5) or prolyl endopeptidase activity (PEP, EC 3.4.21.26) activity was detectable (<5 µU/µg). Alkaline phosphatase and sucrase were used as control BBM enzymes with activities of 66 µU/µg and 350 µU/µg, respectively.

BBM fractions were partially purified from the small intestinal mucosa of adult female rats maintained on an ad libitum diet of wheat-based standard rodent chow. Total protein content was determined by a modified method of Lowry with BSA as a standard. Alkaline phosphatase activity was determined with nitrophenyl phosphate. Sucrase activity was measured using a coupled glucose assay. DPP IV, proline aminopeptidase and APN were assayed continuously at 30° C. in 0.1 M Tris-HCl, pH 8.0, containing 1 mM of the p-nitroanilides ($\epsilon$=8,800 $M^{-1}$ $cm^{-1}$) Gly-Pro-pNA, Pro-pNA or Leu-pNA, the latter in additional 1% DMSO to improve solubility. DCP activity was measured in a 100 µl reaction as the release of hippuric acid from Hip-His-Leu. PEP activity was determined continuously with 0.4 mM Z-Gly-Pro-pNA in PBS: $H_2O$:dioxane (8:1.2:0.8) at 30° C. One unit is defined as the consumption of 1 µmol substrate per minute.

DPP IV and DCP are both up-regulated by a high proline content in the diet. However, APN activity using standard substrates was found to be higher than DPP IV even when fed extreme proline rich diets. Also, although a higher DCP vs. CPP activity has been observed with the model peptide Z-GPLAP at saturating concentrations, a difference in Km values could easily account the reversed ratio measured in this study. 100 µM was chosen as the initial peptide concentration, since non-saturating kinetics ($k_{cat}/K_m$) were considered to be physiologically more relevant than the maximal rates of hydrolysis ($k_{cat}$).

Proteolysis with the BBM preparation was investigated using the peptide (SEQ ID NO:1) QLQPFPQPQLPY, a product of chymotryptic digestion of α-9 gliadin (Arentz-Hansen et al. (2000) *J. Exp. Med.* 191, 603-12). This peptide has been shown to stimulate proliferation of T cells isolated from most Celiac Sprue patients, and hence is considered to possess an immunodominant epitope. It was subjected to BBM digestion, followed by LC-MS-MS analysis. A standard 50 µl digestion mixture contained 100 µM of synthetic peptide, 10 µM tryptophan and Cbz-tryptophan as internal standards, and resuspended BBM preparations with a final prot in content of 27 ng/µl and exogenous proteins, as indicated, in phosphate buffered saline. After incubation at 37° C. for the indicated time, the enzymes were inactivated by heating to 95° C. for 3 minutes. The reaction mixtures were analyzed by LC-MS (SpectraSystem, ThermoFinnigan) using a C18 reversed phase column (Vydac 218TP5215, 2.1×150 mm) with water: acetonitrile:formic acid (0.1%):trifluoroacetic acid (0.025%) as the mobile phase (flow: 0.2 ml/min) and a gradient of 10% acetonitrile for 3 minutes, 10-20% for 3 minutes, 20-25% for 21 minutes followed by a 95% wash. Peptide fragments in the mass range of m/z=300-2000 were detected by electrospray ionization mass spectroscopy using a LCQ ion trap, and their identities were confirmed by MSMS fragmentation patterns.

While the parent peptide (SEQ ID NO:1) QLQPFPQPQLPY disappeared with an apparent halftime of 35 min, several intermediates were observed to accumulate over prolonged periods (FIG. 1A). The MS intensities (m/z=300-2000 g/mol) and $UV_{280}$ absorbances of the parent peptides (SEQ ID NO:1) QLQPFPQPQLPY and (SEQ ID NO:3)

PQPQLPYPQPQLPY were found to depend linearly on concentration in the range of 6-100 µM. The reference peptides (SEQ ID NO:4) PQPQLPYPQPQLP, (SEQ ID NO:5) QLQPFPQPQLP, (SEQ ID NO:6) QPQFPQPQLPY and (SEQ ID NO:7) QPFPQPQLP were generated individually by limited proteolysis of the parent peptides with 10 µg/ml carboxypeptidase A (C-0261, Sigma) and/or 5.9 µg/ml leucine aminopeptidase (L-5006, Sigma) for 160 min. at 37° C. and analyzed by LC-MS as in FIG. 1.

Indeed, the subsequent processing of the peptide was substantially retarded (FIG. 1B). The identities of the major intermediates were confirmed by tandem MS, and suggested an unusually high degree of stability of the (SEQ ID NO:8) PQPQLP sequence, a common motif in T cell stimulating peptides. Based on this data and the known amino acid preferences of the BBM peptidases, the digestive breakdown of (SEQ ID NO:1) QLQPFPQPQLPY was reconstructed, as shown in the insert of FIG. 1B. The preferred pathway involves serial cleavage of the N-terminal glutamine and leucine residues by aminopeptidase N (APN), followed by removal of the C-terminal tyrosine by carboxypeptidase P (CPP) and hydrolysis of the remaining N-terminal QP-dipeptide by DPP IV. As seen in FIG. 1B, the intermediate (SEQ ID NO:6) QPFPQPQLPY (formed by APN attack on the first two N-terminal residues) and its derivatives are increasingly resistant to further hydrolysis. Because the high proline content seemed to be a major cause for this proteolytic resistance, digestion was compared with a commercially available non-proline control peptide (SEQ ID NO:9) RRLIEDNEYTARG (Sigma, St. Louis, Mo.). Initial hydrolysis was much faster ($t_{1/2}$=10 min). More importantly, digestive intermediates were only transiently observed and cleared completely within one hour, reflecting a continuing high specificity of the BBM for the intermediate peptides.

Because the three major intermediate products (SEQ ID NO:6) QPFPQPQLPY, (SEQ ID NO:7) QPFPQPQLP, (SEQ ID NO:11) FPQPQLP) observed during BBM mediated digestion of (SEQ ID NO:1) QLQPFPQPQLPY are substrates for DPP IV, the experiment was repeated in the presence of a 6-fold excess activity of exogenous fungal DPP IV. Whereas the relatively rapid decrease of the parent peptide and the intermediate levels of (SEQ ID NO:5) QLQPFPQPQLP were largely unchanged, the accumulation of DPP IV substrates was entirely suppressed and complete digestion was observed within four hours. (FIG. 1B, open bars).

Figure 2A:
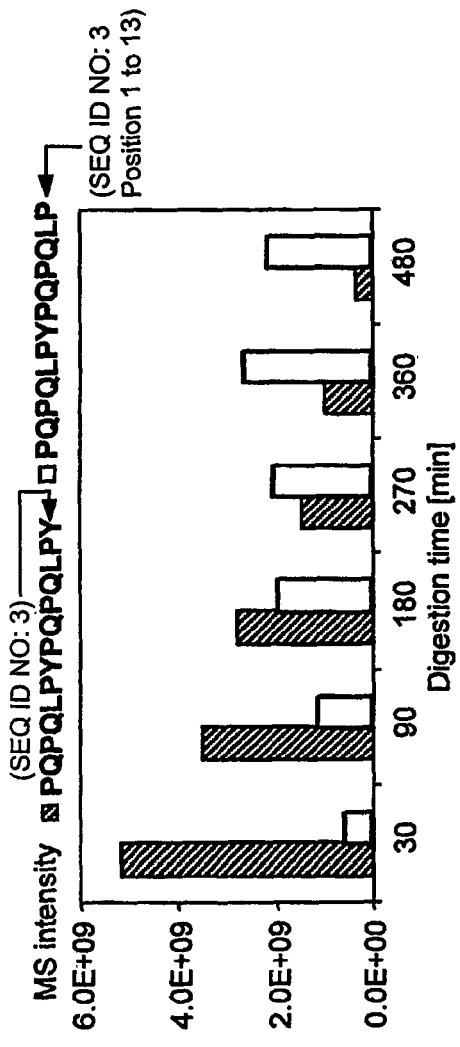
FIGS. 2A-2B. C-terminal digestion of the immunodominant gliadin peptide by brush border membrane.
Figure 2B:
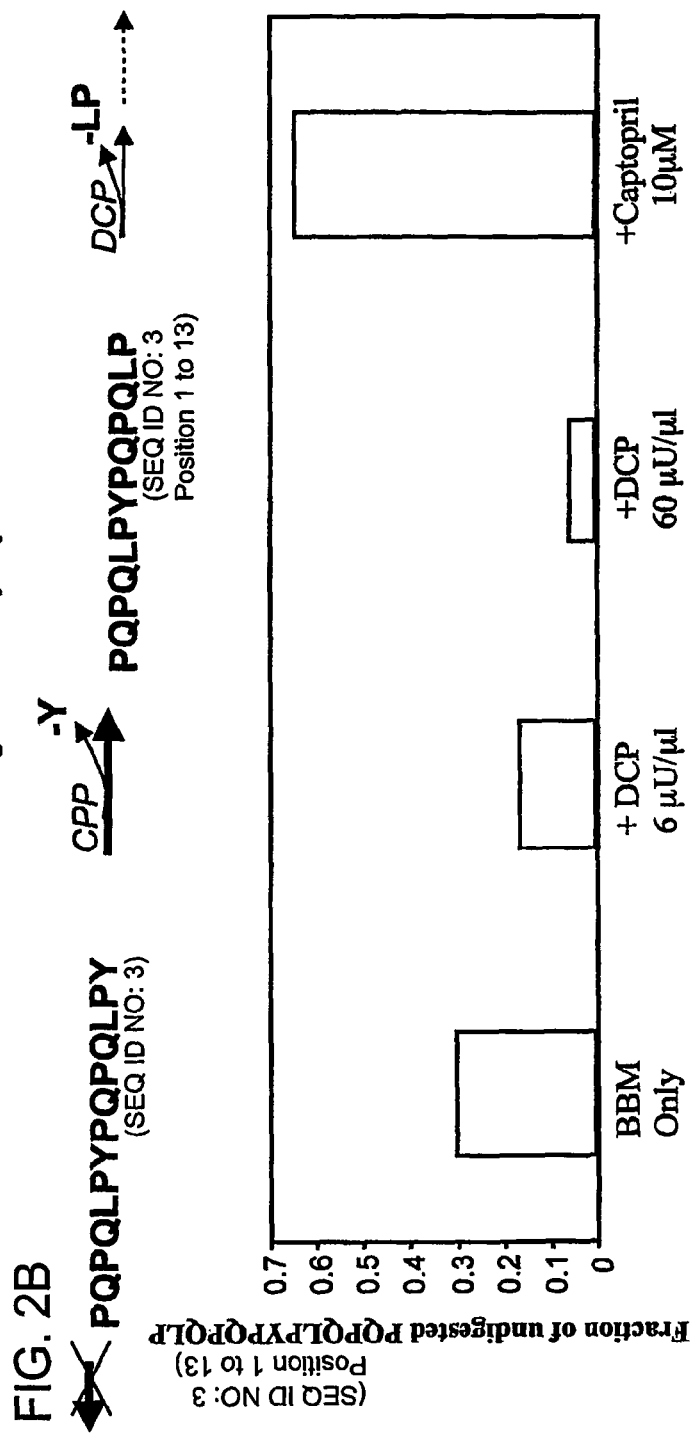
Figure 3:
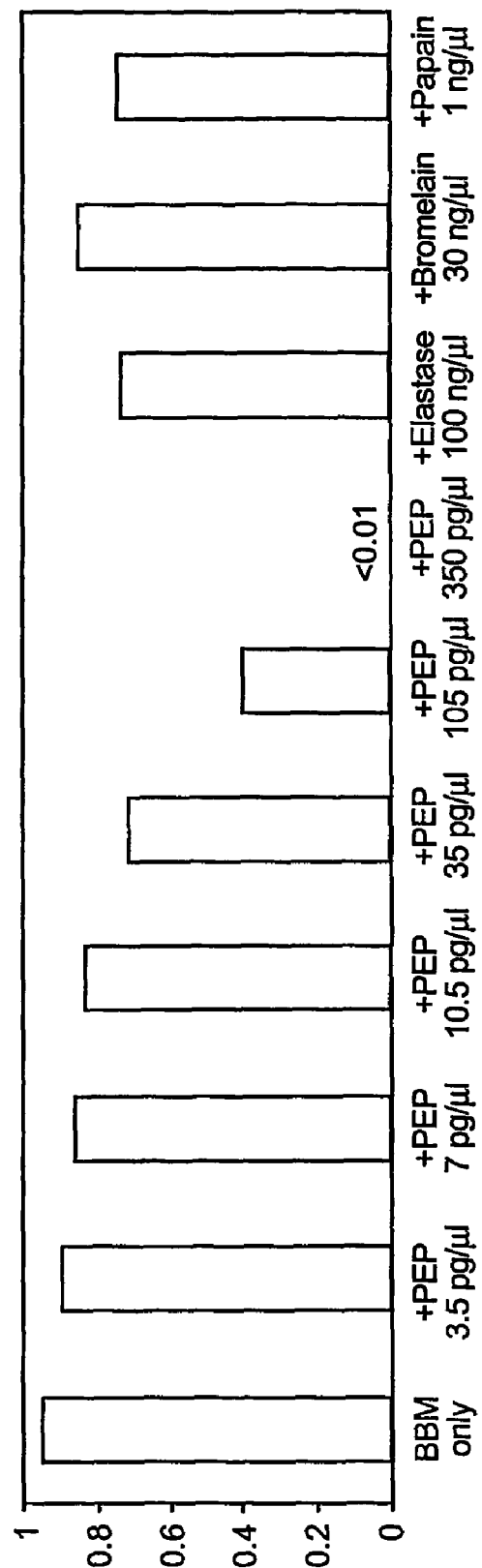
FIG. 3. Dose dependent acceleration of brush border mediated digestion by exogenous endoproteases. As seen from FIG. 2A-2B, the peptide (SEQ ID NO:4) PQPQLPYPQPQLP is stable toward further digestion. This peptide was digested with 27 ng/µl brush border membranes, either alone, with increasing amounts of exogenous prolyl endopeptidase (PEP, specific activity 28 µU/pg) from *Flavobacterium meningosepticum* (US Biological, MA), or with additional elastase (E-1250, Sigma, MO), bromelain (B-5144, Sigma, MO) or papain (P-5306, Sigma, MO). After one hour, the fraction of remaining (SEQ ID NO:4) PQPQLPYPQPQLP (compared to the initial amount at t=0 min) was analyzed and quantified as in FIG. 1.

To investigate the rate-limiting steps in BBM mediated digestion of gliadin peptides from the C-terminal end, another known immunodominant peptide derived from wheat α-gliadin, (SEQ ID NO:3) PQPQLPYPQPQLPY, was used. Although peptides with N-terminal proline residues are unlikely to form in the small intestine (none were observed during BBM digestion of (SEQ ID NO:1) QLQPFPQPQLPY, FIG. 1A), they serve as a useful model for the analysis of C-terminal processing since the N-terminal end of this peptide can be considered proteolytically inaccessible due to minimal proline aminopeptidase activity in the BBM. As shown in FIG. 2, this peptide is even more stable than (SEQ ID NO:1) QLQPFPQPQLPY. In particular, removal of the C-terminal tyrosine residue by carboxypeptidase P (CPP) is the first event in its breakdown, and more than four times slower than APN activity on (SEQ ID NO:1) QLQPFPQPQLPY (FIG. 1B). The DCP substrate (SEQ ID NO:4) PQPQLPYPQPQLP emerges as a major intermediate following carboxypeptidase P catalysis, and is highly resistant to further digestion, presumably due to the low level of endogenous DCP activity naturally associated with the BBM. To confirm the role of DCP as a rate-limiting enzyme in the C-terminal processing of immunodominant gliadin peptides, the reaction mixtures were supplemented with rabbit lung DCP. Exogenous DCP significantly reduced the accumulation of (SEQ ID NO:4) PQPQLPYPQPQLP after overnight incubation in a dose dependent manner (FIG. 2C). Conversely, the amount of accumulated (SEQ ID NO:4) PQPQLPYPQPQLP increased more than 2-fold in the presence of 10 µM of captopril, a DCP-specific inhibitor, as compared with unsupplemented BBM.

Together, the above results demonstrate that (i) immunodominant gliadin peptides are exceptionally stable toward breakdown catalyzed by BBM peptidases, and (ii) DPP IV and especially DCP are rate-limiting steps in this breakdown process at the N- and C-terminal ends of the peptides, respectively. Because BBM exopeptidases are restricted to N- or C-terminal processing, it was investigated if generation of additional free peptide ends by pancreatic enzymes would accelerate digestion. Of the pancreatic proteases tested, only elastase at a high (non-physiological) concentration of 100 ng/µl was capable of hydrolyzing (SEQ ID NO:3) PQPQLPYPQPQ↓LPY. No proteolysis was detected with trypsin or chymotrypsin.

The above data demonstrates that proline-rich gliadin peptides are extraordinarily resistant to digestion by small intestinal endo- and exopeptidases, and therefore are likely to accumulate at high concentrations in the intestinal cavity after a gluten rich meal. The pathological implication of digestive resistance is strengthened by the observed close correlation of proline content and celiac toxicity as observed in the various common cereals (Schuppan (2000) Gastroenterology 119, 234-42).

EXAMPLE 2

Immunodominant Peptide of Wheat Gliadin

It has long been known that the principal toxic components of wheat gluten are a family of closely related Pro-Gin rich proteins called gliadins. Recent reports have suggested that peptides from a short segment of α-gliadin appear to account for most of the gluten-specific recognition by CD4+ T cells from Celiac Sprue patients. These peptides are substrates of tissue transglutaminase (tTGase), the primary auto-antigen in Celiac Sprue, and the products of this enzymatic reaction bind to the class II HLA DQ2 molecule. This example demonstrates, using a combination of in vitro and in vivo animal and human studies, that this "immunodominant" region of α-gliadin is part of an unusually long proteolytic product generated by the digestive process that: (a) is exceptionally resistant to further breakdown by gastric, pancreatic and intestinal brush border proteases; (b) is the highest specificity substrate of human tissue transglutaminase (tTGase) discovered to date; (c) contains at least six overlapping copies of epitopes known to be recognized by patient derived T cells; (d) stimulates representative T cell clones that recognize these epitopes with sub-micromolar efficacy; and (e) has homologs in proteins from all toxic foodgrains but no homologs in non-toxic foodgrain proteins. In aggregate, these findings demonstrate that the onset of symptoms upon gluten exposure can be traced back to a small segment of α-gliadin. Finally, it is shown that this "super-antigenic" long peptide can be detoxified in vitro and in vivo by treatment with bacterial prolyl endopeptidase, providing a strategy for peptidase therapy for Celiac Sprue.

Identification of stable peptides from gastric protease, pancreatic protease and brush border membrane peptidase catalyzed digestion of recombinant α2-gliadin: α2-gliadin, a representative α-gliadin (Arentz-Hansen et al. (2000) Gut 46:46), was expressed in recombinant form and purified from *E. coli.* The α2-gliadin gene was cloned in pET28a plasmid (Novagen) and transformed into the expression host BL21 (DE3) (Novagen). The transformed cells were grown in 1-liter cultures of LB media containing 50 µg/ml of kanamycin at 37° C. until the OD600 0.6-1 was achieved. The expression of α2-gliadin protein was induced with the addition of 0.4 mM isopropyl β-D-thiogalactoside (Sigma), and the cultures were further incubated at 37° C. for 20 hours. The cells expressing the recombinant α2-gliadin were centrifuged at 3600 rpm for 30 minutes. The pellet was resuspended in 15 ml of disruption buffer (200 mM sodium phosphate; 200 mM NaCl; 2.5 mM DTT; 1.5 mM benzamidine; 2.5 mM EDTA; 2 mg/L pepstatin; 2 mg/L leupeptin; 30% v/v glycerol) and lysed by sonication (1 minute; output control set to 6). After centrifugation at 45000 g for 45 min, the supernatant was discarded and the pellet containing gliadin protein was resuspended in 50 ml of 7M urea in 50 mM Tris (pH=8.0). The suspension was again centrifuged at 45000 g for 45 min and the supernatant was harvested for purification.

The supernatant containing α2-gliadin was incubated with 1 ml of nickel-nitrilotriacetic acid resin (Ni-NTA; Qiagen) overnight and then batch-loaded on a column with 2 ml of Ni-NTA. The column was washed with 7 M urea in 50 mM Tris (pH=8.0), and α2-gliadin was eluted with 200 mM imidazole, 7 M urea in 50 mM Tris (pH=4.5). The fractions containing α2-gliadin were pooled into a final concentration of 70% ethanol solution, and two volumes of 1.5 M NaCl were added to precipitate the protein. The solution was incubated at 4° C. overnight, and the final precipitate was collected by centrifugation at 45000 g for 30 min., rinsed in water, and re-centrifuged to remove the urea. The final purification step of the α-2 gliadin was developed with reverse-phase HPLC. The Ni-NTA purified protein fractions were pooled in 7 M urea buffer and injected to a Vydac (Hesperia, CA) polystyrene reverse-phase column (i.d. 4.6 mm×25 cm) with the starting solvent (30% of solvent B: 1:1 HPLC-grade acetonitrile/isopropanol:0.1% TFA). Solvent A was an aqueous solution with 0.1% TFA. The separation gradient extended from 30-100% of solvent B over 120 min. at a flow rate of 0.8 ml/min.

TABLE 2

Amount of Peptides Digested after 15 hours

|  | 33-mer | Control A | Control B |
| --- | --- | --- | --- |
| H1P0 | <20% | >90% | >90% |
| H2P0 | <20% | >61% | >85% |
| H3P0 | <20% | >87% | >95% |
| H4P0 | <20% | >96% | >95% |
| H5P0 | <20% | >96% | >95% |

The purity of the recombinant gliadin was >95%, which allowed for facile identification and assignment of proteolytic products by LC-MS/MS/UV. Although many previous studies utilized pepsin/trypsin treated gliadins, it was found that, among gastric and pancreatic proteases, chymotrypsin played a major role in the breakdown of α2-gliadin, resulting in many small peptides from the C-terminal half of the protein and a few longer (>8 residues) peptides from the N-terminal half, the most noteworthy being a relatively large fragment, the 33-mer (SEQ ID NO:12) LQLQPF-PQPQLPYPQPQLPYPQPQLPYPQPQPF (residues 57-89). This peptide was of particular interest for two reasons: (a) whereas most other relatively stable proteolytic fragments were cleaved to smaller fragments when the reaction times were extended, the 33-mer peptide remained intact despite prolonged exposure to proteases; and (b) three distinct patient-specific T cell epitopes identified previously are present in this peptide, namely, PFPQPQLPY, PQPQLPYPQ (3 copies), and PYPQPQLPY (2 copies).

Figure 4:
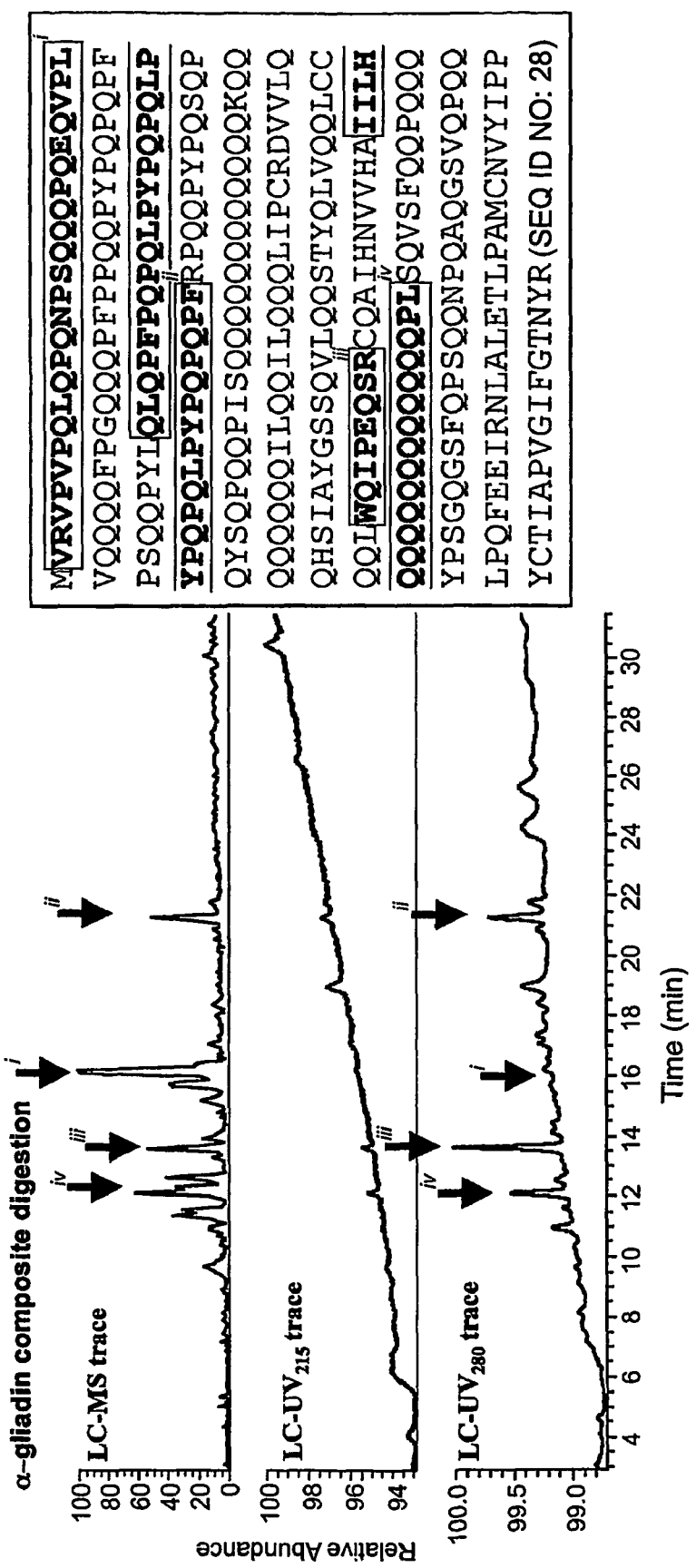
FIG. 4. Products of gastric and pancreatic protease mediated digestion of α2-gliadin under physiological conditions. Analysis was performed by LC-MS. The longest peptides are highlighted by arrows and also in the sequence of α2-gliadin (inset).
Figure 5:
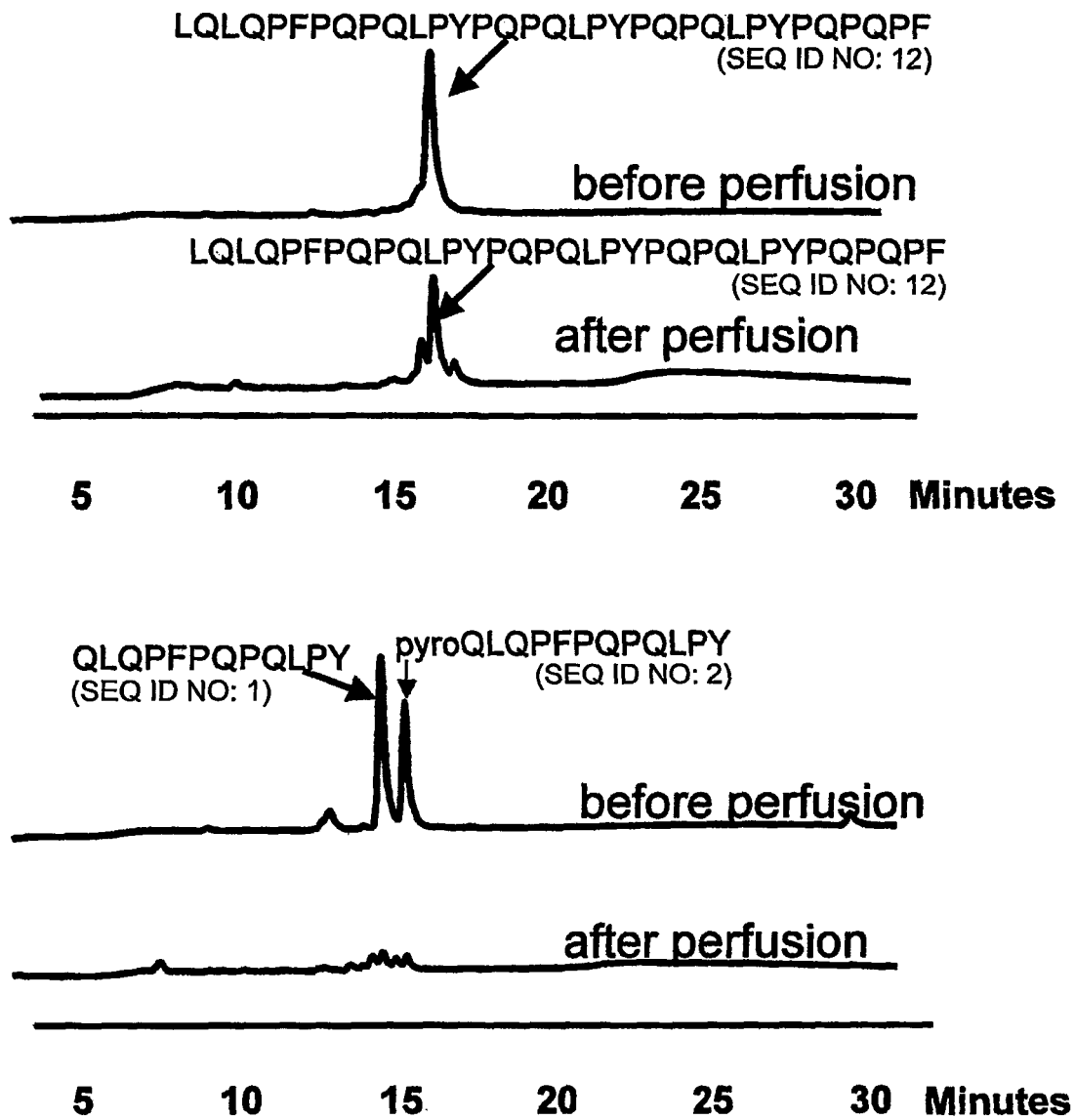
FIG. 5. In vivo brush border membrane digestion of peptides. LC-$UV_{215}$ traces of 25 µM of (SEQ ID NO:12) LQLQPFPQPQLPYPQPQLPYPQPQLPYPQPQPF before perfusion and after perfusion (residence time=20 min). LC-$UV_{215}$ traces of 50 µM of (SEQ ID NO:1) QLQPFPQPQLPY before perfusion and after perfusion (residence time=20 min).

To establish the physiological relevance of this peptide, composite gastric/pancreatic enzymatic digestion of α2 gliadin was then examined. As expected, enzymatic digestion with pepsin (1:100 w/w ratio), trypsin (1:100), chymotrypsin (1:100), elastase (1:500) and carboxypeptidase (1:100) was quite efficient, leaving behind only a few peptides longer than 9 residues (the minimum size for a peptide to show class II MHC mediated antigenicity) (FIG. 4). In addition to the above-mentioned 33-mer, the peptide WQIPEQSR was also identified, and was used as a control in many of the following studies. The stability of the 33-mer peptide can also be appreciated, when comparing the results of a similar experiment using myoglobin (another common dietary protein). Under similar proteolytic conditions, myoglobin is rapidly broken down into much smaller products. No long intermediate is observed to accumulate.

The small intestinal brush-border membrane (BBM) enzymes are known to be vital for breaking down any remaining peptides from gastric/pancreatic digestion into amino acids, dipeptides or tripeptides for nutritional uptake. Therefore a comprehensive analysis of gliadin metabolism also required investigations into BBM processing of gliadin peptides of reasonable length derived from gastric and pancreatic protease treatment. BBM fractions were prepared from rat small intestinal mucosa. The specific activities of known BBM peptidases were verified to be within the previously reported range. Whereas the half-life of disappearance of WQIPEQSR was ~60 min. in the presence of 12 ng/µl BBM protein, the half-life of (SEQ ID NO:12) LQLQPF-PQPQLPYPQPQLPYPQPQLPYPQPQPF digestion was >20 h. Therefore, the latter peptide remains intact throughout the digestive process in the stomach and upper small intestine, and is poised to act as a potential antigen for T cell proliferation and intestinal toxicity in genetically susceptible individuals.

Verification of proteolytic resistance of the 33-mer gliadin peptide with brush border membrane preparations from human intestinal biopsies: To validate the above conclusions, derived from studies with rat BBM preparations, in the context of human intestinal digestion, BBM preparations were prepared from a panel of adult human volunteers, one of whom was a Celiac Sprue patient in remission, while the rest were found to have normal intestinal histology. (SEQ ID NO:12) LQLQPFPQPQLPYPQPQLPYP QPQLPYPQPQPF, (SEQ ID NO:1) QLQPFPQPQLPY (an internal sequence from the 33-mer used as a control), WQIPEQSR and other control peptides (100 µM) were incubated with BBM prepared from each human biopsy (final aminopeptidase N activity of 13 µU/µl) at 37° C. for varying time periods. While QLQPFPQPQLPY, WQIPEQSR and other control peptides were completely proteolyzed within 1-5 h, the long peptide remained largely intact for at 19 hours. These results confirm the equivalence between the rat and human BBM for the purpose of this study.

Verification of proteolytic resistance of the 33-mergliadin peptide in intact animals: The proteolytic resistance of the 33-mer gliadin peptide, observed in vitro using BBM from rats and humans, was confirmed in vivo using a perfusion protocol in intact adult rats (Smithson and Gray (1977) *J. Clin. Invest.* 60:665). Purified peptide solutions were perfused through a 15-20 cm segment of jejunum in a sedated rat with a residence time of 20 min., and the products were collected and subjected to LC-MS analysis. Whereas >90% of (SEQ ID NO:1) QLQPFPQPQLPY was proteolyzed in the perfusion experiment, most of the 33-mer gliadin peptide remained intact. These results demonstrate that the 33-mer peptide is very stable as it is transported through the mammalian upper small intestine.

The 33-mer gliadin peptide is an excellent substrate for tTGase, and the resulting product is a highly potent activator of patient-derived T cells. A number of recent studies have demonstrated that regiospecific deamidation of immunogenic gliadin peptides by tTGase increases their affinity for HLA-DQ2 as well as the potency with which they activate patient-derived gluten-specific T cells. It has been shown the specificity of tTGase for certain short antigenic peptides derived from gliadin is higher than its specificity toward its physiological target site in fibronectin, for example, the specificity of tTGase for the α-gliadin derived peptide PQPQLPYPQPQLPY is 5-fold higher than that for its target peptide sequence in fibrinogen, its natural substrate. The kinetics and regiospecificity of deamidation of the 33-mer α-gliadin peptide identified as above were therefore measured. The $k_{cat}/K_M$ was higher than that reported for any peptide studied thus far: kcat/KM=440 min-1 mM-1 for (SEQ ID NO:12) LQLQPFPQPQLPYPQPQLPYPQPQLPYPQPQPF compared to kcat/KM=82 min-1mM-1 for PQPQLPY and kcat/KM=350 min-1 mM-1 for PQPQLPYPQPQLPY.

Moreover, LC-MS-MS analysis revealed that (SEQ ID NO:12) LQLQPFPQPQLPYPQPQLPYPQPQLPYPQPQPF was selectively deamidated by tTGase at the underlined residues. Since tTGase activity is associated with the brush border membrane of intestinal enterocytes, it is likely that dietary uptake of even small quantities of wheat gluten will lead to the build-up of sufficient quantities of this 33-mer gliadin peptide in the intestinal lumen so as to be recognized and processed by tTGase.

Figure 6:
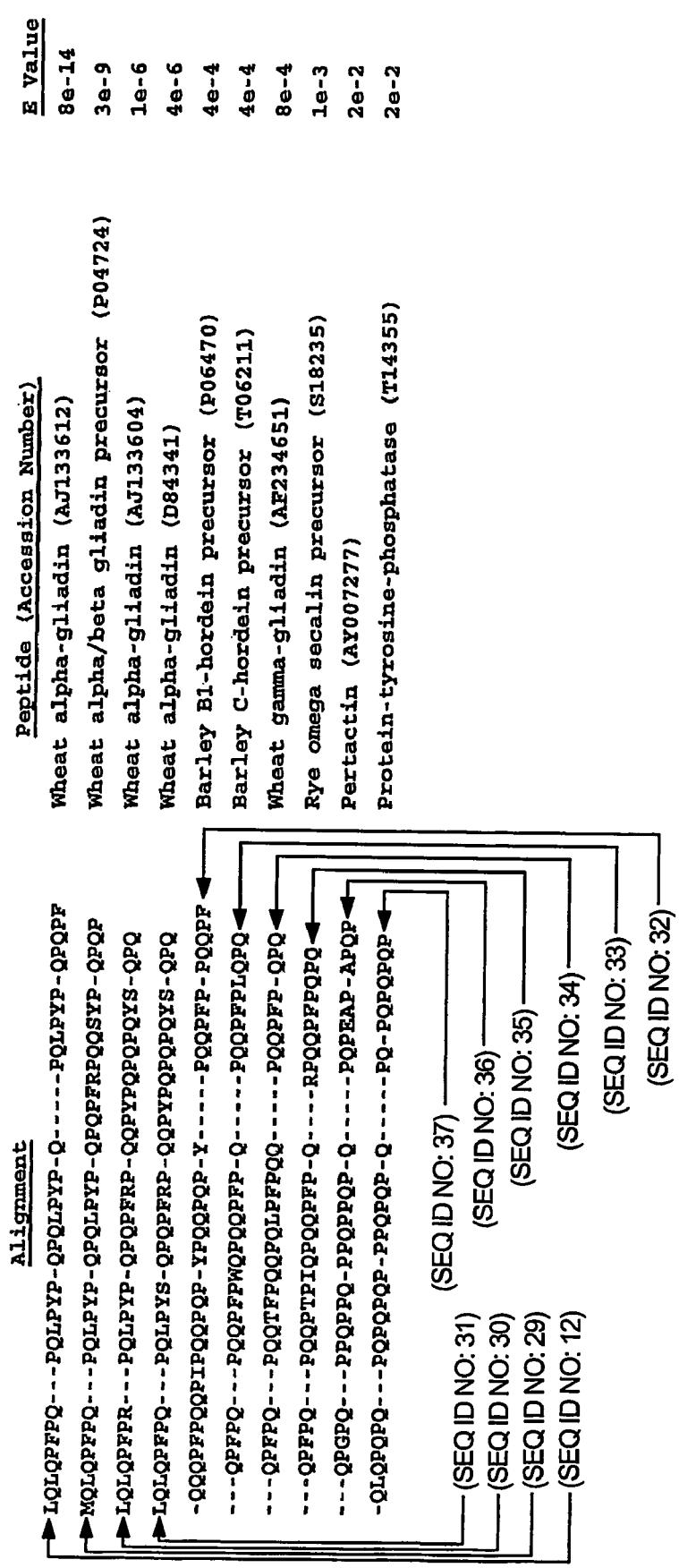
FIG. 6. Alignment of representative gluten and non-gluten peptides homologous to (SEQ ID NO:12) LQLQPFPQPQLPYPQPQLPYPQPQLPYPQPQPF.
Figure 7:
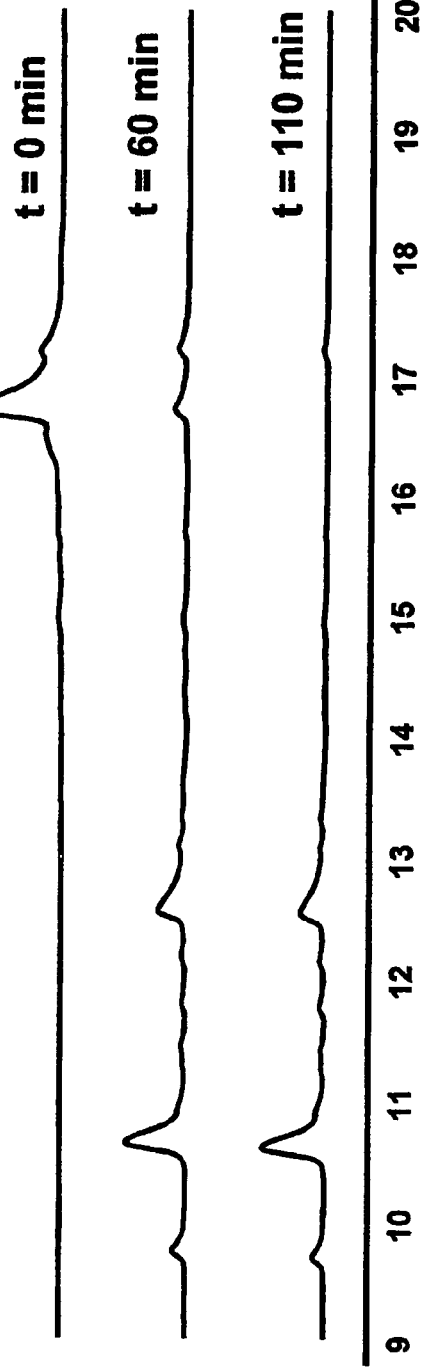
FIG. 7. Breakdown and detoxification of 33-mer gliadin peptide with PEP. In vitro incubation of PEP (540 mU/ml) with the 33-mer gliadin peptide (100 µM) for the indicated time. In vivo digestion of the 33-mer gliadin peptide (25 µM) with PEP (25 mU/ml) and the rat's intestine (residence time=20 min).
Figure 7:
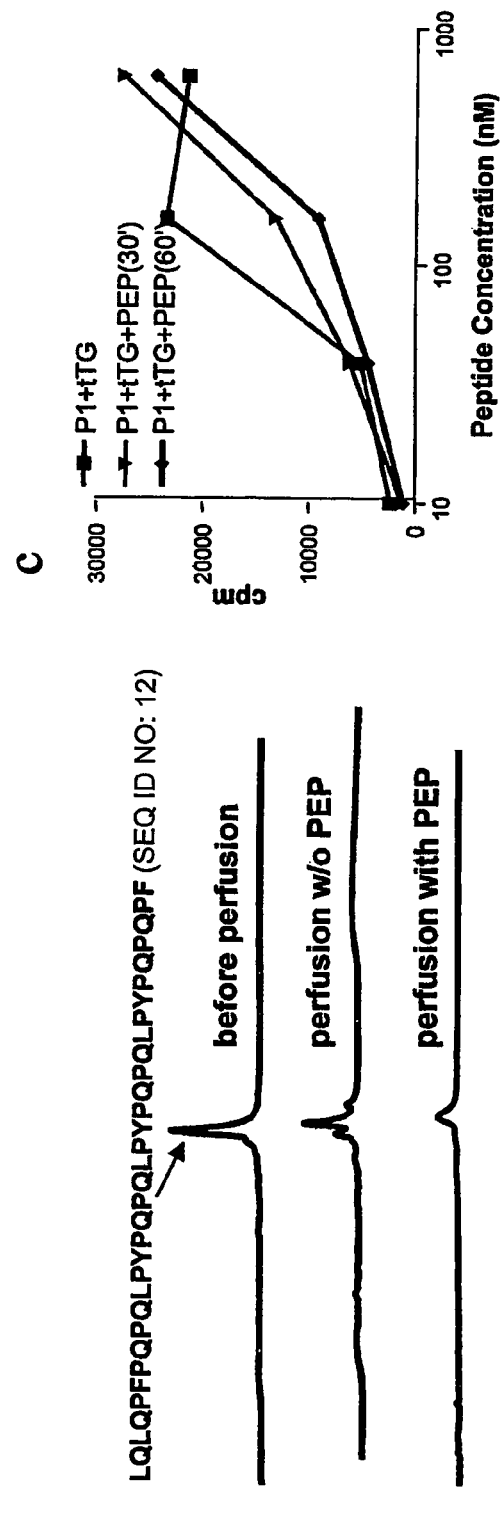

Structural characteristics of the 33-mer gliadin peptide and its naturally occurring homologs: Sequence alignment searches using BLASTP in all non-redundant protein databases revealed several homologs (E-value <0.001) of the 33-mer gliadin peptide. Interestingly, foodgrain derived homologs were only found in gliadins (from wheat), hordeins (from barley) and secalins (from rye), all of which have been proven to be toxic to Celiac patients. See FIG. 6. Nontoxic foodgrain proteins, such as avenins (in oats), rice and maize, do not contain homologous sequences to the 33-mer gliadin. In contrast, a BLASTP search with the entire α2-gliadin sequence identified foodgrain protein homologs from both toxic and nontoxic proteins. Based on available information regarding the substrate specificities of gastric, pancreatic and BBM proteases and peptidases, it is predicted that, although most gluten homologs to the 33-mer gliadin peptide contained multiple proteolytic sites and are therefore unlikely to be completely stable toward digestion, several sequences from wheat, rye and barley are expected to be comparably resistant to gastric and intestinal proteolysis. The stable peptide homologs to the 33-mer α2-gliadin peptide are QPQPF-PPQLPYPQTQPFPPQQPYPQPQPQYPQPQ (from α1- and α6-gliadins); QQQPF-PQQPIPQQPQPYPQQPQPYPQQPFPPQQPF (from B1 hordein); QPFPQPQQTFPQQPQLPFPQQPQQPFPQPQ (from γ-gliadin); QPFPQPQQPTPIQPQQPFPQRPQQPF-PQPQ (from ω-secalin). These stable peptides are all located at the N-terminal region of the corresponding proteins. The presence of proline residues after otherwise cleavable residues in these peptides would contribute to their proteolytic stability.

The unique primary sequence of the 33-mer gliadin peptide also had homologs among a few non-gluten proteins. Among the strongest homologs were internal sequences from pertactin (a highly immunogenic protein from *Bordetella pertussis*) and a mammalian inositol-polyphosphate 5-phosphatase of unknown function. In both cases available information suggested that the homology could have biologically relevance. For example, the region of pertactin that is homologous to the 33-mer gliadin peptide is known to be part of the immunodominant segment of the protein. In the case of the homologous phosphatase, the corresponding peptide region of the phosphatase is known to be responsible for vesicular trafficking of the phosphatase to the cytoplasmic Golgi. In analogy with the current picture of how gliadin peptides are presented to HLA-DQ2 via a tTGase mediated pathway, these Pro-Gin-rich segments of both pertactin and the phosphatase are likely to be good tTGase substrates. To test this hypothesis, the corresponding peptides were synthesized, and the selectivity of tTGase for these peptides was measured. As predicted, both peptides were found to be good substrates of tTGase. The tTGase enzyme plays a central role in receptor mediated endocytosis of several biologically important proteins. The biological activities of both pertactin and the phosphatase may depend on tTGase mediated trafficking.

Secondary structural studies using circular dichroism spectroscopy on the 33-mer gliadin peptide as well as its homologs from pertactin and the inositol-polyphosphate 5-phosphatase demonstrate that these peptides have strong type II polyproline helical character. In addition to reinforcing the proteolytic resistance of these peptides, the type II polyproline helical conformation is also likely to enhance their affinity for class II MHC proteins.

Although gluten proteins from foodgrains such as wheat, rye and barley are central components of a nutritious diet, they can be extremely toxic for patients suffering from Celiac Sprue. To elucidate the structural basis of gluten toxicity in Celiac Sprue, comprehensive proteolytic analysis was performed on a representative recombinant gliadin under physiologically relevant conditions. An unusually long and proteolytically stable peptide product was discovered, whose physiological relevance was confirmed by studies involving brush border membrane proteins from rat and human intestines as well as intestinal perfusion assays in live rats. In aggregate, these data demonstrate that this peptide and its homologs found in other wheat, rye and barley proteins are the "root cause" of the initial inflammatory response to dietary wheat in Celiac Sprue patients in remission.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in protein structure without affecting the biological action in kind or amount. All such modifications are intended to be included within the scope of the appended claims.

What is claimed is:

1. A method of generating an antibody-producing cell line; the method comprising:

immunizing an animal with a purified oligopeptide having the amino acid sequence LQLQPF-PQPQLPYPQPQLPYPQPQLPYPQPQPF (SEQ ID NO:12) to generate a cell line producing an antibody that binds specifically to a said purified oligopeptide having the amino acid sequence LQLQPF-PQPQLPYPQPQLPYPQPQLPYPQPQPF (SEQ ID NO:12).

2. An antibody produced by the cell line producing by the method of claim 1.

3. The antibody of claim 2, wherein the antibody is a polyclonal antibody.

4. The antibody of claim 2, wherein the antibody is a monoclonal antibody.

5. An antibody is produced by a cell line generated by a response to a tissue transglutaminase linked to SEQ ID NO:12 that binds specifically to said tissue transglutaminase linked to SEQ ID NO:12.

6. An antibody producing cell line that that was generated by an immune response to a tissue transglutaminase linked to SEQ ID NO:12.

* * * * *

UNITED STATES PATENT AND TRADEMARK OFFICE
CERTIFICATE OF CORRECTION

PATENT NO. : 7,776,545 B2  Page 1 of 1
APPLICATION NO. : 10/531547
DATED : August 17, 2010
INVENTOR(S) : Chaitan Khosla It is certified that error appears in the above-identified patent and that said Letters Patent is hereby corrected as shown below:

In the Claims:

Claim 5, Column 38, line 19: Delete the word "is"

Signed and Sealed this
Twenty-sixth Day of July, 2011

David J. Kappos
*Director of the United States Patent and Trademark Office*

SEQUENCE LISTING

<160> NUMBER OF SEQ ID NOS: 26

<210> SEQ ID NO 1
<211> LENGTH: 12
<212> TYPE: PRT
<213> ORGANISM: Triticum aestivum

<400> SEQUENCE: 1

Gln Leu Gln Pro Phe Pro Gln Pro Gln Leu Pro Tyr
1               5                   10

<210> SEQ ID NO 2
<211> LENGTH: 12
<212> TYPE: PRT
<213> ORGANISM: Triticum aestivum
<220> FEATURE:
<221> NAME/KEY: PYRROLIDONE CARBOXYLIC ACID
<222> LOCATION: (1)...(1)
<223> OTHER INFORMATION: N terminal pyroglutaminate

<400> SEQUENCE: 2

Gln Leu Gln Pro Phe Pro Gln Pro Gln Leu Pro Tyr
1               5                   10

<210> SEQ ID NO 3
<211> LENGTH: 14
<212> TYPE: PRT
<213> ORGANISM: Triticum aestivum

<400> SEQUENCE: 3

Pro Gln Pro Gln Leu Pro Tyr Pro Gln Pro Gln Leu Pro Tyr
1               5                   10

<210> SEQ ID NO 4
<211> LENGTH: 13
<212> TYPE: PRT
<213> ORGANISM: Triticum aestivum

<400> SEQUENCE: 4

Pro Gln Pro Gln Leu Pro Tyr Pro Gln Pro Gln Leu Pro
1               5                   10

<210> SEQ ID NO 5
<211> LENGTH: 11
<212> TYPE: PRT
<213> ORGANISM: Triticum aestivum

<400> SEQUENCE: 5

Gln Leu Gln Pro Phe Pro Gln Pro Gln Leu Pro
1               5                   10

<210> SEQ ID NO 6
<211> LENGTH: 11
<212> TYPE: PRT
<213> ORGANISM: Triticum aestivum

<400> SEQUENCE: 6

Gln Pro Gln Phe Pro Gln Pro Gln Leu Pro Tyr
1               5                   10

<210> SEQ ID NO 7
<211> LENGTH: 9
<212> TYPE: PRT
<213> ORGANISM: Triticum aestivum

```
<400> SEQUENCE: 7

Gln Pro Phe Pro Gln Pro Gln Leu Pro
1               5

<210> SEQ ID NO 8
<211> LENGTH: 6
<212> TYPE: PRT
<213> ORGANISM: Triticum aestivum

<400> SEQUENCE: 8

Pro Gln Pro Gln Leu Pro
1               5

<210> SEQ ID NO 9
<211> LENGTH: 13
<212> TYPE: PRT
<213> ORGANISM: Triticum aestivum

<400> SEQUENCE: 9

Arg Arg Leu Ile Glu Asp Asn Glu Tyr Thr Ala Arg Gly
1               5                   10

<210> SEQ ID NO 10
<211> LENGTH: 9
<212> TYPE: PRT
<213> ORGANISM: Triticum aestivum

<400> SEQUENCE: 10

Pro Phe Pro Gln Pro Gln Leu Pro Tyr
1               5

<210> SEQ ID NO 11
<211> LENGTH: 7
<212> TYPE: PRT
<213> ORGANISM: Triticum aestivum

<400> SEQUENCE: 11

Phe Pro Gln Pro Gln Leu Pro
1               5

<210> SEQ ID NO 12
<211> LENGTH: 33
<212> TYPE: PRT
<213> ORGANISM: Triticum aestivum

<400> SEQUENCE: 12

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
                20                  25                  30

Phe

<210> SEQ ID NO 13
<211> LENGTH: 34
<212> TYPE: PRT
<213> ORGANISM: Triticum aestivum

<400> SEQUENCE: 13

Gln Pro Gln Pro Phe Pro Pro Gln Leu Pro Tyr Pro Gln Thr Gln Pro
1               5                   10                  15

Phe Pro Pro Gln Gln Pro Tyr Pro Gln Pro Gln Pro Gln Tyr Pro Gln
                20                  25                  30
```

Pro Gln

<210> SEQ ID NO 14
<211> LENGTH: 35
<212> TYPE: PRT
<213> ORGANISM: Triticum aestivum

<400> SEQUENCE: 14

Gln Gln Gln Pro Phe Pro Gln Gln Pro Ile Pro Gln Gln Pro Gln Pro
1               5                   10                  15

Tyr Pro Gln Gln Pro Gln Pro Tyr Pro Gln Gln Pro Phe Pro Pro Gln
            20                  25                  30

Gln Pro Phe
        35

<210> SEQ ID NO 15
<211> LENGTH: 30
<212> TYPE: PRT
<213> ORGANISM: Triticum aestivum

<400> SEQUENCE: 15

Gln Pro Phe Pro Gln Pro Gln Gln Thr Phe Pro Gln Gln Pro Gln Leu
1               5                   10                  15

Pro Phe Pro Gln Gln Pro Gln Gln Pro Phe Pro Gln Pro Gln
            20                  25                  30

<210> SEQ ID NO 16
<211> LENGTH: 59
<212> TYPE: PRT
<213> ORGANISM: Triticum aestivum

<400> SEQUENCE: 16

Pro Gln Gln Pro Gln Leu Pro Phe Pro Gln Gln Pro Gln Gln Pro Phe
1               5                   10                  15

Pro Gln Pro Gln Gln Pro Gln Gln Pro Phe Pro Gln Ser Gln Gln Pro
            20                  25                  30

Gln Gln Pro Phe Pro Gln Pro Gln Gln Gln Phe Pro Gln Pro Gln Gln
        35                  40                  45

Pro Gln Gln Ser Phe Pro Gln Gln Gln Pro
    50                  55

<210> SEQ ID NO 17
<211> LENGTH: 30
<212> TYPE: PRT
<213> ORGANISM: Triticum aestivum

<400> SEQUENCE: 17

Gln Pro Phe Pro Gln Pro Gln Gln Pro Thr Pro Ile Gln Pro Gln Gln
1               5                   10                  15

Pro Phe Pro Gln Arg Pro Gln Gln Pro Phe Pro Gln Pro Gln
            20                  25                  30

<210> SEQ ID NO 18
<211> LENGTH: 9
<212> TYPE: PRT
<213> ORGANISM: Triticum aestivum

<400> SEQUENCE: 18

Pro Gln Pro Gln Leu Pro Tyr Pro Gln
1               5

```
<210> SEQ ID NO 19
<211> LENGTH: 9
<212> TYPE: PRT
<213> ORGANISM: Triticum aestivum

<400> SEQUENCE: 19

Pro Gln Leu Pro Tyr Pro Gln Pro Gln
1               5

<210> SEQ ID NO 20
<211> LENGTH: 9
<212> TYPE: PRT
<213> ORGANISM: Triticum aestivum

<400> SEQUENCE: 20

Pro Tyr Pro Gln Pro Gln Leu Pro Tyr
1               5

<210> SEQ ID NO 21
<211> LENGTH: 9
<212> TYPE: PRT
<213> ORGANISM: Triticum aestivum

<400> SEQUENCE: 21

Pro Gln Pro Glu Leu Pro Tyr Pro Gln
1               5

<210> SEQ ID NO 22
<211> LENGTH: 9
<212> TYPE: PRT
<213> ORGANISM: Triticum aestivum

<400> SEQUENCE: 22

Pro Phe Pro Gln Pro Glu Leu Pro Tyr
1               5

<210> SEQ ID NO 23
<211> LENGTH: 9
<212> TYPE: PRT
<213> ORGANISM: Triticum aestivum

<400> SEQUENCE: 23

Pro Gln Gln Ser Phe Pro Gln Gln Gln
1               5

<210> SEQ ID NO 24
<211> LENGTH: 11
<212> TYPE: PRT
<213> ORGANISM: Triticum aestivum

<400> SEQUENCE: 24

Pro Phe Pro Gln Gln Pro Gln Gln Pro Phe Pro
1               5                   10

<210> SEQ ID NO 25
<211> LENGTH: 9
<212> TYPE: PRT
<213> ORGANISM: Triticum aestivum

<400> SEQUENCE: 25

Pro Tyr Pro Gln Pro Glu Leu Pro Tyr
1               5

<210> SEQ ID NO 26
```

```
-continued

<211> LENGTH: 27
<212> TYPE: PRT
<213> ORGANISM: Triticum aestivum

<400> SEQUENCE: 26

Pro Phe Pro Gln Pro Gln Leu Pro Tyr Pro Phe Pro Gln Pro Gln Leu
1               5                   10                  15

Pro Tyr Pro Phe Pro Gln Pro Gln Leu Pro Tyr
            20              25
```